(12) United States Patent
Chou et al.

(10) Patent No.: US 8,119,170 B2
(45) Date of Patent: *Feb. 21, 2012

(54) HERBAL COMPOSITIONS AND METHODS FOR ENHANCING VITAL ENERGY AND ATHLETIC PERFORMANCE

(76) Inventors: Wen Hsien Chou, Kowloon (HK); Vivien Chou, Kowloon (HK)

( * ) Notice: Subject to any disclaimer, the term of this patent is extended or adjusted under 35 U.S.C. 154(b) by 0 days.

This patent is subject to a terminal disclaimer.

(21) Appl. No.: 12/957,195

(22) Filed: Nov. 30, 2010

(65) Prior Publication Data

US 2011/0091585 A1    Apr. 21, 2011

Related U.S. Application Data

(63) Continuation of application No. 12/426,035, filed on Apr. 17, 2009, now Pat. No. 7,906,159.

(60) Provisional application No. 61/045,717, filed on Apr. 17, 2008.

(51) Int. Cl.
*A61K 36/16*    (2006.01)
*A61K 36/00*    (2006.01)

(52) U.S. Cl. .......................................... 424/752; 424/773

(58) Field of Classification Search .................. None
See application file for complete search history.

(56) References Cited

U.S. PATENT DOCUMENTS

| | | | |
|---|---|---|---|
| 4,444,879 A * | 4/1984 | Foster et al. | 435/7.95 |
| 7,303,772 B2 | 12/2007 | Rangel et al. | |
| 7,906,159 B2 | 3/2011 | Chou et al. | |
| 2002/0127285 A1* | 9/2002 | Xiu | 424/725 |
| 2003/0008048 A1 | 1/2003 | Winston et al. | |
| 2004/0234544 A1 | 11/2004 | Jager et al. | |
| 2008/0031978 A1 | 2/2008 | Chou | |
| 2009/0317497 A1 | 12/2009 | Chou et al. | |

FOREIGN PATENT DOCUMENTS

| | | |
|---|---|---|
| CN | 1077896 | 11/1993 |
| CN | 1216683 | 5/1999 |
| CN | 1363371 A | 8/2002 |
| CN | 1395850 | 2/2003 |
| CN | 1522747 A | 8/2004 |
| CN | 1628845 A | 6/2005 |
| CN | 1651009 A | 8/2005 |
| CN | 1686469 A | 10/2005 |
| CN | 1895601 | 1/2007 |
| CN | 1931217 A | 3/2007 |
| CN | 1977876 | 6/2007 |
| CN | 1977878 A | 6/2007 |
| JP | 9000229 | 1/1997 |
| KR | 2001016591 A | 3/2001 |
| RU | 2077219 | 4/1997 |
| WO | WO 2006/021930 A2 | 3/2006 |
| WO | WO 2006/021930 A3 | 5/2006 |

OTHER PUBLICATIONS

Kelly, G. S. Rhodiola rosea: a possible plant adaptogen. Altern Med Rev. Jun. 2001;6(3):293-302.
International search report dated Aug. 16, 2007 for PCT Application No. CN07/001296.
International search report dated Sep. 30, 2010 for PCT Application No. IB2010/001014.

* cited by examiner

*Primary Examiner* — Michele Flood
*Assistant Examiner* — Deborah A. Davis
(74) *Attorney, Agent, or Firm* — Wilson, Sonsini, Goodrich & Rosati

(57) ABSTRACT

Compositions, kits and methods are provided for enhancing vital energy and athletic performance, improving or restoring blood circulation, promoting mental acuity, reducing fatigue, and improving aerobic performance. In one embodiment, the composition comprises the herbal extracts of *Rhodiola crenulata* (root) and *Ginkgo biloba* (leaf). The composition can be used as a pharmaceutical or nutraceutical to promote mental concentration, and to promote aerobic and anaerobic performance by enhancing strength, endurance, muscle tissue oxygenation, and optimal oxygen consumption.

19 Claims, 10 Drawing Sheets

HERBAL COMPOSITIONS AND METHODS FOR ENHANCING VITAL ENERGY AND ATHLETIC PERFORMANCE

CROSS-REFERENCE

This application is a continuation of U.S. application Ser. No. 12/426,035, filed Apr. 17, 2009, which claims the benefit of U.S. Provisional Application No. 61/045,717, filed Apr. 17, 2008, each of which is incorporated herein by reference.

BACKGROUND

In Chinese Medicine, physical exercise has a close relationship with vital energy ("qi", also known as "chi") health. In Chinese Medicine movements of the muscles and the four limbs are believed to depend on the power of the vital energy—qi. When the internal vital energy is sufficient, the limbs and muscles are healthy and strong because they are nourished by the blood and qi. If the internal vital energy is deficient however, the muscles become weak, resulting in feelings of tiredness and general malaise.

Vital energy plays an important role in supporting physical activities of the body. During intense periods of physical exercise, especially endurance types, there are great demands on muscle energy and also cardiovascular and pulmonary functions. In Chinese Medicine, these are all closely related to the vital energy—qi of the body. Lung qi is responsible for pulmonary functions while heart qi is responsible for cardiovascular function. Physical activities, including the limb movements, on the other hand, are mainly coordinated by spleen qi. Therefore, the body's physical performance is closely linked with having an adequate amount of vital energy so that the organs can communicate and work efficiently with one another.

Intense physical exercise can easily exhaust the body's energy stores and consume vital energy. In order to maintain continuous performance in physical exercise, it is important to pay attention to the recovery of vital energy. Adequate rest is essential. If exhaustion is so severe that the body is unable to recover, an individual can develop a certain degree of deficiency of qi and vital energy, which may manifest as fatigue, lack of energy and unsatisfactory performance of physical activities. If the deficiency is very severe or persists for a long time, it can even affect a person's overall health because vital energy is also responsible for the majority of physiological activities in the body.

Balance between vital energy health and physical exercise is very important. If there is an optimal balance, physical exercise can benefit the health of the whole body because it promotes blood and qi circulation, which in turn supports vital energy health. On the other hand, if physical exercise is too intense, it can deplete the energy reserve of the body and exhaust the vital energy which over time may then result in health problems. Therefore, to maintain health and reach optimal physical performance, new methods of improving the body's recovery after exercise are desirable, especially to improve the recovery of the vital energy.

SUMMARY

The present disclosure provides novel compositions, kits and methods for pharmaceutical or nutraceutical use in a mammal, preferably in a human.

In one aspect, compositions are provided, comprising an herbal extract of *Rhodiola crenulata* and an herbal extract of *Ginkgo biloba*. The composition may further comprise one or more excipients. The composition may be a solid, liquid, or an aerosol.

In some embodiments, the herbal extract of *Rhodiola crenulata* comprises at least about 0.40%, at least about 0.50%, at least about 0.60%, at least about 0.70%, at least about 0.80%, or at least about 0.90% w/w salidroside based on the total weight of the herbal extract.

In some embodiments, the herbal extract of *Ginkgo biloba* comprises at least about 5.0%; at least about 6.0%, at least about 7.0%, at least about 8.0%, at least about 9.0%, at least about 10.0%, at least about 11.0%, at least about 12.0%, at least about 13.0%; or at least about 14.0% w/w flavonoids based on the total weight of the herbal extract.

In some embodiments, the herbal extract of *Rhodiola crenulata* comprises about 5-95% w/w of the total weight of the composition. In some of the embodiments, the herbal extract of *Ginkgo biloba* comprises about 5-50% w/w of the total weight of the composition. In some embodiments, the herbal extract of *Rhodiola crenulata* comprises about 50-95% w/w and the herbal extract of *Ginkgo biloba* comprises about 5-50% w/w of the total weight of the composition.

In some embodiments, the herbal extract of *Rhodiola crenulata* is about 90% w/w and the herbal extract of *Ginkgo biloba* is about 10% w/w of the total weight of the composition. In other embodiments, the herbal extract of *Rhodiola crenulata* is about 45-70% w/w and the herbal extract of *Ginkgo biloba* is about 5-10% w/w of the total weight of the composition.

In another aspect of the present disclosure, a method for improving or restoring blood circulation in the body of a mammal is provided, comprising administering to a mammal in need thereof an effective amount of the composition described herein. The mammal is preferably a human, more preferably an athlete, and most preferably a professional athlete.

In yet another aspect, a method for promoting mental acuity in a mammal is provided, comprising administering to the mammal in need thereof an effective amount of the composition described herein. The mammal may be a pet animal, but preferably a human.

In a further aspect of the disclosure, a method for reducing fatigue in a mammal is provided, comprising administering to the mammal in need thereof an effective amount of the composition of the present disclosure. The mammal is preferably a human.

In another aspect, a method for promoting aerobic and anaerobic sports performance in a mammal is provided, comprising administering to the mammal in need thereof an effective amount of the composition disclosed herein. The mammal is preferably a human, more preferably an athlete, and most preferably a professional athlete.

In some embodiments, the administration of compositions disclosed herein to a mammal is via an oral route. In some embodiments, the composition is administered to a mammal at a dose of about 1-2600 mg/day, more preferably about 400-2000 mg/day, even more preferably about 800-1600 mg/day, even more preferably about 1200-1600 mg/day, and most preferably about 1000 mg/day. In some embodiments, multiple daily doses of 50, 100, 200, 300, 400, 500, 600, 700, 800 or more mg per dose are provided.

In some embodiments, the composition is orally administered to a mammal at a daily dose of about 1-100 mg/kg, more preferably at about 5-50 mg/kg, even more preferably about 10-30 mg/kg, and most preferably about 20-25 mg/kg. Lower doses of about 1-6 mg/kg or about 1-5 mg/kg may be provided. Multiple daily doses may include 2, 3, 4, 5, 6, 7, 8, 9, 10, or more doses. In various embodiments directed to oral administration disclosed herein, the mammal is a human.

In another aspect, a kit is provided, comprising: a container containing at least one dose of an effective amount of the composition disclosed herein. In some embodiments, the kit further comprises instructions of how to use the kit to improve or restore blood circulation, promote mental acuity, reduce fatigue, or promote aerobic performance. In some embodiments, the kit comprises more than one dose of an effective amount of the composition disclosed herein.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1:
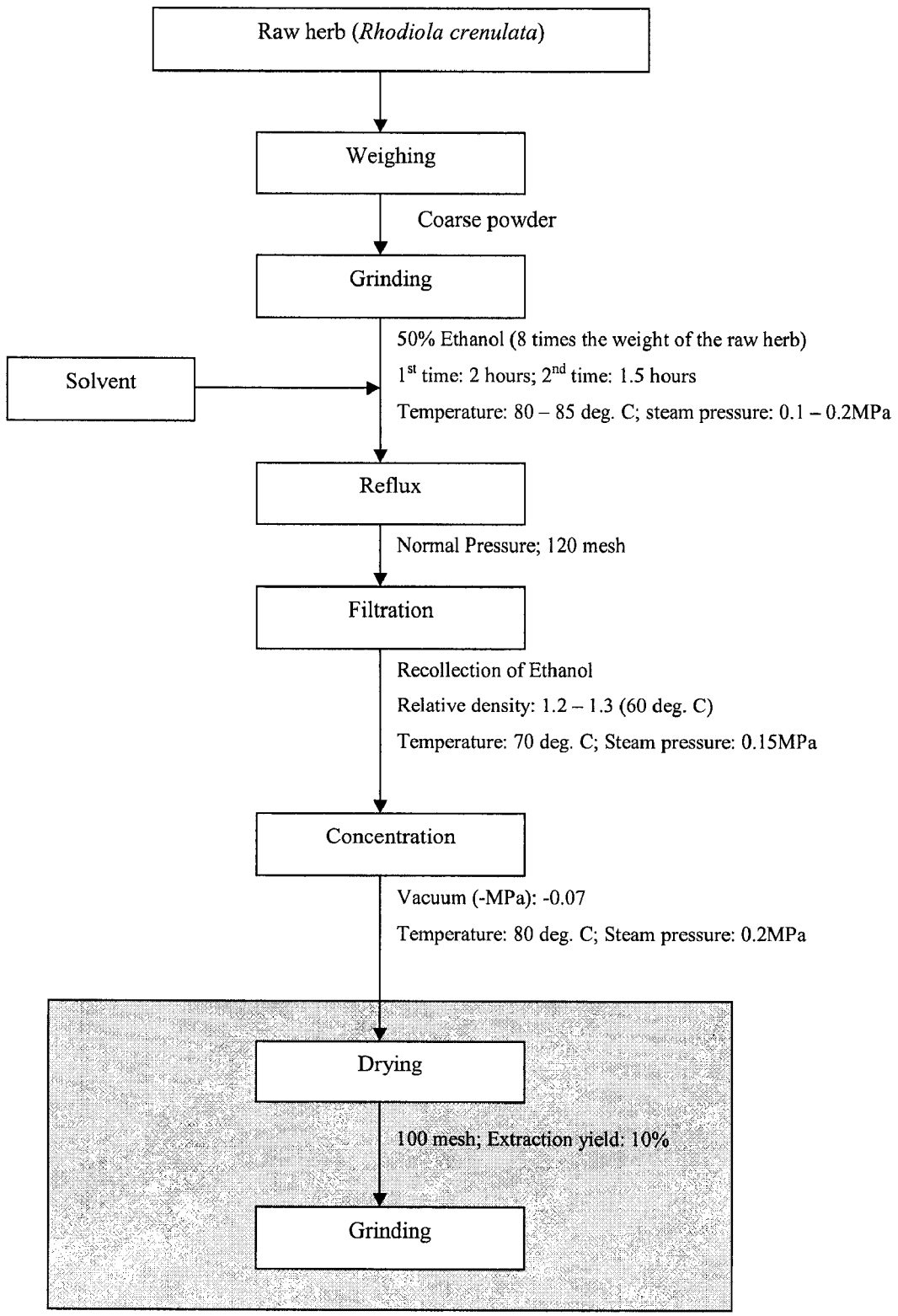
FIG. 1 is a flow chart representing an extraction process for *Rhodiola creulata*.

The present disclosure provides novel compositions for nutraceutical or pharmaceutical use in a mammal, preferably in a human. In some embodiments, the composition comprises the herbal extract of *Rhodiola crenulata* at about 50-90% w/w and the herbal extract of *Ginkgo biloba* at about 5-30% w/w based on the total weight of the extract combination. Any combination of proportions of the herbal extracts of *Rhodiola crenulata* and *Gingko biloba* are envisioned to be encompassed by the compositions disclosed herein. In one embodiment, the composition is a combination of *Rhodiola crenulata* (root) at about 90% w/w and *Ginkgo biloba* (leaves) at about 10% w/w based on the total weight of the herbal extract components of the composition. The percentages provided herein refer to the w/w ratio based on the total weight of the herbal extract portion of the composition and do not include any excipients of extra ingredients added to a formulation.

In one aspect, compositions are provided which comprise an herbal extract of *Rhodiola crenulata* and an herbal extract of *Ginkgo biloba*. The combination of these herbal extracts may enhance their functions compared to that when administered alone. Therefore, the combination synergizes the activity of the herbal extracts, as well as decreases one or more toxic effects of the constituent herbs. Compositions of the present disclosure may be, for example, solid, liquid, or aerosol formulations comprising one or more of the extracts as disclosed herein. Compositions of the disclosure may also comprise other components, for example, vitamins, pharmaceuticals or excipients.

Folium *Ginkgo* consists of the dried whole leaf of *Ginkgo biloba*. *Ginkgo biloba* is thought to have neuroprotective properties; however, the exact neuroprotective mechanism of *Ginkgo biloba* is not known, but *Ginkgo biloba* herbal extract components include flavone glycosides (which is made up of quercetin, kaempferol, rutin and myricetin) as well as terpene lactones (ginkgolides A and B), all of which decrease free radical release. In addition, terpene lactones have been shown to improve blood flow and reduce thrombus formation by inhibiting platelet-activating factor. Without being bound by any one theory, one mechanism of action by which compounds of the disclosure functions is by removing free radicals which cause oxidative damage to tissue. For example, *Ginkgo biloba* may reduce or prevent cell membrane lipid peroxidation, decrease oxidative damage to red blood cells and protect nerve cells. Thus, *Ginkgo biloba* herbal extract may benefit any cell or tissue that can be damaged by free radicals. In one embodiment, the *Ginkgo biloba* herbal extract portion reduces or prevents oxidative damage in the central nervous system and vasculature by improving blood flow and circulation.

Further, *Ginkgo biloba* is a well-known memory-improving agent that has been widely used in aged people and patients with memory problems (Birks et al., *Cochrane Database Syst. Rev.* 18:CD003120, (2007); Schulz, *Phytomedicine* 10(S): 74-79, (2003)). Moreover, *Ginkgo biloba* extracts are also used for preventing acute mountain sickness (Gertsch et al., *High Alt. Med. Biol.* 3:29-37, (2002); Gertsch et al., *BMJ.* 328:797, (2004)) and relieving the symptoms of intermittent claudication (Pittler & Ernst, *Am. J. Med.* 108:276-281, (2000)), suggesting that *Ginkgo biloba* may have a capacity to improve mental conditions and physical work performance.

The *Rhodiola* used in the compositions of the present disclosure can be isolated from any species of *Rhodiola*. Preferably, the *Rhodiola* used is an extract isolated from the dried root and rhizome of *Rhodiola crenulata*. *Rhodiola* is a high altitude growing plant and there are about 200 species, including *R. rosea* and *R. crenulata* (Kelly, *Altern. Med. Rev.* 6:293-302, (2001); Ming et al., *Phytother. Res.* 19:740-743, (2005)). *Rhodiola crenulata* is a Tibetan plant which grows at altitudes greater than 3500 meters. *Rhodiola crenulata* is an adaptogen which helps the body adapt to and resist a variety of physical, chemical, and environmental stresses. Therefore, in various embodiments, compositions of the disclosure may be used to increase energy, stamina, strength, and mental capacity. In further embodiments, compositions of the disclosure may help to reduce fatigue and prevent altitude sickness. In one embodiment, compositions of the disclosure administered to a mammal comprise *Rhodiola crenulata* extract. One bioactive ingredient of interest in *Rhodiola crenulata* is salidroside. Rosavins is another bioactive constituent identified from the plant. Salidroside and/or rosavins can be used as references for determination of the quality of the preparations.

Furthermore, one aspect of the disclosure comprises a composition comprising a combined preparation from *Rhodiola crenulata* and *Ginkgo biloba* leaf. Such compositions may possess robust adaptogenic and ergogenic effects. Such compositions can be manufactured in various formulations, which are administered to a mammal to promote resilience to environmental stressors such as increased oxygen demand or reduced oxygen availability, pollutants, time zone changes, lack of sleep, or enhance energy production.

*Rhodiola crenulata* and *Ginkgo biloba* may be extracted with alcohol, water, or alcohol/water and the extracts can be concentrated, and dried to solid form, such as in the form of a powder. Each may undergo a single, or alternatively, double extraction process. In a preferred embodiment, *Rhodiola crenulata* (root) is extracted with alcohol (ethanol), concentrated, and dried to yield yellowish brown powder with thin odor and bitter taste. In a preferred embodiment, *Rhodiola crenulata* (root) may go through an extraction process twice, each time with alcohol and water. *Ginkgo biloba* (leaf) may be extracted with water/alcohol, concentrated, and dried to yield light brownish yellow powder with thin odor and bitter taste. One of skill in the art will recognize that multiple processes of preparing plant extracts and can be used for the present disclosure, in addition to the particular processes disclosed herein. See, e.g., U.S. Pat. No. 6,996,919.

In some embodiments, a composition of the disclosure comprises an herbal extract of *Rhodiola crenulata* containing a desired amount of about 0.01%, about 0.05%, about 0.10%, about 0.15%, about 0.20%, about 0.25%, about 0.30%, about 0.35%, about 0.40%, about 0.45%, about 0.50%, about 0.55%, about 0.60%, about 0.65%, about 0.70%, about 0.75%, about 0.80%, about 0.85%, about 0.90%, about 0.95%, about 1.00%, about 1.05%, about 1.10%, about 1.15%, about 1.20%, about 1.25%, about 1.30%, about 1.35%, about 1.40%, about 1.45%, about 1.50%, about 1.55%, about 1.60%, about 1.65%, about 1.70%, about 1.75%, about 1.80%, about 1.85%, about 1.90%, about 1.95%, or about 2.00% salidroside w/w of the total weight of the extract. In some embodiments, compositions of the present disclosure comprise an extract of *Rhodiola crenulata* comprising 1-5% salidroside w/w of the total weight of the extract. More preferably, the extracts comprise 1-2% salidroside, and most preferably, the extracts comprise 1.2-1.7% salidroside w/w of the total weight of the extract.

In some embodiments, a composition of the disclosure comprises an herbal extract of *Ginkgo biloba* comprising not less than about 0.5%, about 1.0%, about 1.5%, about 2.0%, about 2.5%, about 3.0%, about 3.5%, about 4.0%, about 4.5%, about 5.0%, about 6.0%, about 6.5%, about 7.0%, about 7.5%, about 8.0%, about 8.5%, about 9.0%, about 9.5%, about 10.0%, about 10.5%, about 11.0%, about 11.5%, about 12.0%, about 12.5%, about 13.0%, about 13.5%, about 14.0%, about 14.5%, about 15.0%, about 15.5%, about 16.0%, about 16.5%, about 17.0%, about 17.5%, about 18.0%, about 18.5%, about 19.0%, about 19.5%, about 20.0%, about 20.5%, about 21.0%, about 21.5%, about 22.0%, about 22.5%, about 23.0%, about 23.5%, about 24.0%, about 24.5%, about 25.0%, about 25.5%, about 26.0%, about 26.5%, about 270.0%, about 27.50%, about 28.0%, about 28.50%, about 29.0%, about 29.5%, about 30.0%, about 30.5%, about 31.0%, about 31.5%, about 32.0%, about 32.5%, about 33.0%, about 33.5%, about 34.0%, about 34.5%, about 35.0%, about 35.5%, about 36.0%, about 36.5%, or about 37.0% flavonoids w/w of the total weight of the extract. Preferably, a composition of the disclosure comprises an herbal extract of *Ginkgo biloba* comprising 20-30% flavonoids w/w of the total weight of the extract. Even more preferably, a composition of the disclosure comprises an herbal extract of *Ginkgo biloba* comprising 23-25% flavonoids w/w of the total weight of the extract. Most preferably, a composition of the present disclosure comprises an herbal extract of *Ginkgo biloba* comprising not less than 24% flavonoids w/w of the total weight of the extract.

In some embodiments, a composition of the present disclosure comprises an herbal extract of *Ginkgo biloba* comprising no less than about 0.5%, about 1.0%, about 1.5%, about 2.0%, about 2.5%, about 3.0%, about 3.5%, about 4.0%, about 4.5%, about 5.0%, about 6.0%, about 6.5%, about 7.0%, about 7.5%, about 8.0%, about 8.5%, about 9.0%, about 9.5%, about 10.0%, about 10.5%, about 11.0%, about 11.5%, about 12.0%, about 12.5%, about 13.0%, about 13.5%, about 14.0%, about 14.5%, or about 15.0% of bilobalide ($C_{15}H_{18}O_8$), ginkgolide A ($C_{20}H_{24}O_9$), ginkgolide B ($C_{20}H_{24}O_{10}$), ginkgolide C ($C_{20}H_{24}O_{11}$), referred to as total terpene lactones, of the total weight of the *Ginkgo biloba* extract. Preferably, the compositions of the present disclosure comprise *Ginkgo biloba* extracts comprising no less than 2-10% lactones w/w of the total weight of the extract. More preferably, the compositions of the present disclosure comprise *Ginkgo biloba* extracts comprising no less than 4-9% lactones w/w of the total weight of the extract. Even more preferably, the compositions of the present disclosure comprise *Ginkgo biloba* extracts comprising no less than 5-8% lactones w/w of the total weight of the extract. In yet other preferred embodiments, the compositions comprise *Ginkgo biloba* extracts no less than 6% lactones w/w of the total weight of the extracts. Most preferably, the compositions of the present disclosure comprise *Ginkgo biloba* extracts comprising no less than 5% lactones w/w of the total weight of the extract.

In some embodiments, the compositions of the present disclosure comprise an herbal extract of *Rhodiola crenulata* comprising about 5-95%, about 30-95%, about 40-95%, about 50-95%, about 60-95%, or about 60-90% w/w based on the total weight of the composition. In some embodiments, the compositions of the present disclosure comprise an herbal extract of *Rhodiola crenulata* comprising about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% w/w of the total weight of the composition.

In some embodiments, the compositions of the present disclosure comprise an herbal extract of *Ginkgo biloba* comprising about 5-50%, about 5-40%, about 5-30%, about 5-20% w/w of the total weight of the composition. In some embodiments, the compositions of the present disclosure comprise an herbal extract of *Ginkgo biloba* comprising about 1.0%, about 1.5%, about 2.0%, about 2.5%, about 3.0%, about 3.5%, about 4.0%, about 4.5%, about 5.0%, about 5.5%, about 6.0%, about 6.5%, about 7.0%, about 7.5%, about 8.0%, about 8.5%, about 9.0%, about 9.5%, about 10.0%, about 10.5%, about 11.0%, about 11.5%, about 12.0%, about 12.5%, about 13.0%, about 13.5%, about 14.0%, about 14.5%, about 15.0%, about 15.5%, about 16.0%, about 16.5%, about 17.0%, about 17.5%, about 18.0%, about 18.5%, about 19.0%, or about 20.0% w/w of the total weight of the composition.

After extraction, individual components of the herbal extracts can be mixed into a formulation which can be provided to humans and other animals. In some embodiments, this formulation may be an oral dosage form, including, but not limited to, a pill or tablet. In still further embodiments, these formulations contain 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0 or more mg of salidroside derived from *Rhodiola crenulata*. In still further embodiments, these formulations contain 0.1%, 0.2%, 0.3%, 0.4%, 0.5%, 0.6%, 0.7%, 0.8%, 0.9%, 1.0%, 1.1%, 1.2%, 1.3%, 1.4% or 1.5% salidroside. In some embodiments, these formulations also contain 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 or more mg of flavonoid derived from *Ginkgo biloba*. In still further embodiments, these formulations contain 0.1%, 0.2%, 0.3%, 0.4%, 0.5%, 0.6%, 0.7%, 0.8%, 0.9%, 1.0%, 1.1%, 1.2%, 1.3%, 1.4% or 1.5% flavonoid.

In some embodiments, the herbal components of the composition contain minimal amounts of water. In some embodiments the herbal components contain less than 0.5% of water by weight. In other embodiments, the herbal components of the composition contain less than 0.1% water by weight.

The compositions of the disclosure may further comprise physiologically or pharmaceutically acceptable excipients. Excipients are selected to provide formulations for specific routes of administration and/or preferred types of administration, e.g., administration by tablet, capsule, or liquid dose.

For oral administration, the inventive compositions may optionally be formulated by mixing the herbal ingredients in combination with physiologically or pharmaceutically acceptable carriers that are well known in the art. Such carriers enable the herbal ingredients to be formulated as tablets, pills, dragees, capsules, emulsions, lipophilic and hydrophilic suspensions, liquids, gels, syrups, slurries, suspensions and the like, for oral ingestion by an individual or a patient to be treated.

In one embodiment, the inventive composition is contained in capsules. Capsules suitable for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers.

In some embodiments, a capsule contains about 50-1000 mg, about 100-800 mg, about 150-600 mg, or about 200-400 mg of a mixture of herbal extracts of *Rhodiola crenulata* and *Ginkgo biloba*. In other embodiments, each capsule contains about 50 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg of a mixture of the herbal extracts of *Rhodiola crenulata* and *Ginkgo biloba*. In other embodiments, each capsule contains about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, or about 400 mg of a mixture of the herbal extracts of *Rhodiola crenulata* and *Ginkgo biloba*. In yet other embodiments, each capsule contains about 100 mg, about 110 mg, about 120 mg, about 130 mg, about 140 mg, about 150 mg, about 160 mg, about 170 mg, about 180 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, or about 400 mg of a mixture of the herbal extracts of *Rhodiola crenulata* and *Ginkgo biloba*. In yet other embodiments, each capsule contains about 1000 mg, 100-800 mg, 150-600 mg, or 200-400 mg of a mixture of herbal extracts of *Rhodiola crenulata* and *Ginkgo biloba*.

It is understood that these and other alternate embodiments of the disclosure may include capsules formed of materials besides gelatin such as vegetarian based capsules made from hydroxypropylmethylcellulose.

Optionally, the inventive composition for oral use can be obtained by mixing the inventive composition with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

For buccal administration, the inventive compositions may take the form of tablets or lozenges formulated in conventional manner. Each tablet or lozenge may contain about 50-1000 mg, about 100-800 mg, about 150-600 mg, or about 200-400 mg of a mixture of herbal extracts of *Rhodiola crenulata* and *Ginkgo biloba*. In some embodiments, each tablet or lozenge contains about 50 mg, about 100 mg, about 150 mg, about 200 mg, about 250 mg, about 300 mg, about 350 mg, about 400 mg, about 450 mg, about 500 mg, about 550 mg, or about 600 mg of a mixture of the herbal extracts of *Rhodiola crenulata* and *Ginkgo biloba*. In other embodiments, each tablet or lozenge contains about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, or about 400 mg of a mixture of the herbal extracts of *Rhodiola crenulata* and *Ginkgo biloba*. In yet other embodiments, each tablet or lozenge contains about 100 mg, about 110 mg, about 120 mg, about 130 mg, about 140 mg, about 150 mg, about 160 mg, about 170 mg, about 180 mg, about 200 mg, about 210 mg, about 220 mg, about 230 mg, about 240 mg, about 250 mg, about 260 mg, about 270 mg, about t 280 mg, about 290 mg, about 300 mg, about 310 mg, about 320 mg, about 330 mg, about 340 mg, about 350 mg, about 360 mg, about 370 mg, about 380 mg, about 390 mg, or about 400 mg of a mixture of the herbal extracts of *Rhodiola crenulata* and *Ginkgo biloba*. In yet other embodiments, each tablet or lozenge contains about 1000 mg, 100-800 mg, 150-600 mg, or 200-400 mg of a mixture of herbal extracts of *Rhodiola crenulata* and *Ginkgo biloba*.

For administration by inhalation, the inventive composition for use according to the present disclosure may be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Each dosage unit contains about 50-1000 mg, about 100-800 mg, about 150-600 mg, or about 200-400 mg of a mixture of herbal extracts of *Rhodiola crenulata* and *Ginkgo biloba*. In some embodiments, each dosage unit contains about 50 mg, about 100 mg, about 150 mg, about 200 mg, about 250 mg, about 300 mg, about 350 mg, about 400 mg, about 450 mg, about 500 mg, about 550 mg, or about 600 mg of a mixture of the herbal extracts of *Rhodiola crenulata* and *Ginkgo biloba*. In other embodiments, each dosage unit contains about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, or about 400 mg of a mixture of the herbal extracts of *Rhodiola crenulata* and *Ginkgo biloba*. In yet other embodiments, each dosage unit contains about 100 mg, about 110 mg, about 120 mg, about 130 mg, about 140 mg, about 150 mg, about 160 mg, about 170 mg, about 180 mg, about 200 mg, about 210 mg, about 220 mg, about 230 mg, about 240 mg, about 250 mg, about 260 mg, about 270 mg, about t 280 mg, about 290 mg, about 300 mg, about 310 mg, about 320 mg, about 330 mg, about 340 mg, about 350 mg, about 360 mg, about 370 mg, about 380 mg, about 390 mg, or about 400 mg of a mixture of the herbal extracts of *Rhodiola crenulata* and *Ginkgo biloba*. In yet other embodiments, each dosage unit contains about 1000 mg, about 100-800 mg, about 150-600 mg, or about 200-400 mg of a mixture of herbal extracts of *Rhodiola crenulata* and *Ginkgo biloba*.

Methods of Use

In another aspect of the disclosure, a method of improving or restoring blood circulation is provided. The method of improving or restoring blood circulation comprises administering to a mammal in need thereof, an effective amount of any of the inventive compositions described above. The mammal is preferably a human.

In yet another aspect of the disclosure, a method of promoting mental acuity in a mammal is provided. The method comprises administering to a mammal in need thereof an effective amount of any of the inventive compositions described above. The mammal is preferably a human. By administering a composition of the disclosure, mental acuity and concentration are increased.

In another aspect of the disclosure, a method of reducing fatigue in a mammal is provided. One method of reducing fatigue comprises administering to a mammal in need thereof, an effective amount of any of the inventive compositions described above. The mammal is preferably a human. Fatigue may be the result of exertion in a stressful environment, such as, for example, physical exertion at high altitudes, or may be result of exercise regimes, or extraordinary physical performance. Fatigue may also be the result of performance in a stressful environment such as a fast paced workplace, or travel across time zones, which can be experienced in a non-athletic work situation.

In another aspect of the disclosure, a method of promoting aerobic and anaerobic performance in a mammal is provided. One such method of promoting aerobic and/or anaerobic performance comprises administering to a mammal in need thereof, an effective amount of any of the inventive compositions described above. The mammal is preferably a human. Aerobic performance may be related to exercise, i.e. aerobic exercise or sports performance. Anaerobic performance may be related to high intensity, low duration exertions (e.g., power lifting). Promotion of aerobic and/or anaerobic performance may also be directed towards enhancing muscle tissue and optimizing performance from toned muscle mass. Promotion of aerobic and/or anaerobic performance may also be directed towards improving the strength of muscle mass, or endurance of muscles or overall aerobic endurance, i.e. distance running, skiing, or swimming.

In some of the methods of the present disclosure, a composition is administered orally. In some of the embodiments of the methods of the disclosure, the composition is administered via inhalation or aerosol. The amount of the inventive composition administered will be dependent on the subject being treated, the subject's weight, the manner of administration, and/or the judgment of the prescribing physician. Generally, however, the dosage of the inventive composition will be about 0.01 mg/kg/day to about 1000 mg/kg/day, about 0.01 mg/kg/day to about 500 mg/kg/day, about 1 mg/kg/day to about 600 mg/kg/day, about 5 mg/kg/day to about 500 mg/kg/day, about 7 mg/kg/day to about 300 mg/kg/day, about 10 mg/kg/day to about 150 mg/kg/day, or about 10 mg/kg/day to about 100 mg/kg/day. In some embodiments, the dosage of the inventive composition is about 2-100 mg/kg/day, 5-50 mg/kg/day, 7-40 mg/kg/day, or 8-30 mg/kg/day.

Further, the amount of the herbal extracts administered in the inventive compositions can be about 0.01 mg/kg/day to about 200 mg/kg/day, about 0.01 mg/kg/day to about 100 mg/kg/day, about 1 mg/kg/day to about 50 mg/kg/day, about 5 mg/kg/day to about 30 mg/kg/day, about 7 mg/kg/day to about 20 mg/kg/day, or about 10 mg/kg/day to about 15 mg/kg/day. In some embodiments the daily amount of the herbal extracts administered in the inventive compositions are about 0.1 mg/kg/day, about 0.5 mg/kg/day, about 1.0 mg/kg/day, about 1.5 mg/kg/day, about 2.0 mg/kg/day, about 2.5 mg/kg/day, about 3.0 mg/kg/day, about 4.0 mg/kg/day, about 5.0 mg/kg/day, about 6.0 mg/kg/day, about 7.0 mg/kg/day, about 8.0 mg/kg/day, about 9.0 mg/kg/day, about 10.0 mg/kg/day, about 11.0 mg/kg/day, about 12.0 mg/kg/day, about 13.0 mg/kg/day, about 14.0 mg/kg/day, about 15.0 mg/kg/day, about 16.0 mg/kg/day, about 17.0 mg/kg/day, about 18.0 mg/kg/day, about 19.0 mg/kg/day, about 20.0 mg/kg/day, about 21.0 mg/kg/day, about 22.0 mg/kg/day, about 23.0 mg/kg/day, about 24.0 mg/kg/day, about 25.0 mg/kg/day, about 26.0 mg/kg/day, about 27.0 mg/kg/day, about 28.0 mg/kg/day, about 29.0 mg/kg/day, about 30.0 mg/kg/day, about 31.0 mg/kg/day, about 32.0 mg/kg/day, about 33.0 mg/kg/day, about 34.0 mg/kg/day, about 35.0 mg/kg/day, about 36.0 mg/kg/day, about 37.0 mg/kg/day, about 38.0 mg/kg/day, about 39.0 mg/kg/day, or about 40.0 mg/kg/day.

In some embodiments, the compositions are administered as tablets once or twice a day. In some embodiments, more than one tablet is administered at the same time. In some embodiments, the compositions are administered as lozenges once or twice a day. In some embodiments, more than one lozenge is administered at the same time. In some embodiments, the compositions are administered as capsules once or twice a day. In some embodiments, more than one capsule is administered at the same time. In some embodiments, the compositions are administered as liquid doses once or twice a day. In some embodiments, more than one liquid dose is administered at the same time. In some embodiments, the compositions are administered by inhalation once or twice a day.

In some embodiments of the disclosure, the composition is administered to a human at a dose of about 1-2600 mg/day, more preferably about 400-2000 mg/day, even more preferably about 800-1600 mg/day, even more preferably about 1200-1600 mg/day, and most preferably about 1000 mg/day. In some embodiments, multiple daily doses of 50, 100, 200, 300, 400, 500, 600, 700 or more mg per dose are provided.

In some embodiments of the disclosure, the composition is orally administered to a human at a daily dose of about 1-100 mg/kg, more preferably at about 5-50 mg/kg, even more preferably about 10-30 mg/kg, and most preferably about 20-25 mg/kg. Lower doses of about 1-6 mg/kg or about 1-5 mg/kg may be provided. Multiple daily doses may include 2, 3, 4, 5, 6, 7, 8, 9, 10, or more doses.

For example, to enhance aerobic performance, the dosage of the inventive composition is about 10-100 mg/kg, 20-60 mg/kg, or 30-50 mg/kg once or twice a day. In some embodiments of the methods of the disclosure, the composition is administered to a mammal at a dose of about 1-100 mg/kg, about 1-60 mg/kg, about 1-30 mg/kg, about 1-15 mg/kg, about 1-6 mg/kg or about 1-5 mg/kg once or twice a day. In other embodiments of the methods of the disclosure, the composition is administered to a mammal at a dose of about 10-200 mg/kg, 20-100 mg/kg, or 40-80 mg/kg once or twice a day.

The inventive composition may also be administered in combination with another therapeutic agent (e.g., Losartan, Simvastin, Ramipril, Aspirin, TPA and the like) or nutritional supplement (e.g., Lingzhi, green tea, and/or vitamins) to prevent or treat conditions described above additively or synergistically. The inventive composition may be administered prior to, concomitantly with, or subsequently to the additional therapeutic agent or nutritional supplement.

Kits

The present disclosure also provides a kit or assembly of kits containing the inventive composition. A kit may contain the composition which comprises *Rhodiola crenulata* and *Ginkgo biloba* in a uniform dosage form in a vessel. A kit may also contain a single dosage form or multiple dosage forms. A kit may further comprise a dispensing tool, e.g. a pump, a cup, a spoon, a pipette or eyedropper, and the like. A kit may further comprise instruction as to how to use the kit to promote mental acuity, promote aerobic performance by enhancing strength, endurance, muscle tissue oxygenation, and optimal oxygen consumption, decrease fatigue, and/or promote or restore blood circulation. Instructions may be in a printed form.

Methods of Preparation

*Rhodiola crenulata* Extraction Process.

A schematic version of one process of this extraction process is shown in FIG. 1. The *Rhodiola crenulata* raw herb is weighed and ground into coarse powder. The powder is put into an extraction chamber. Eight-times the total weight of the coarse powder of 50% ethanol is added and the mixture is heated under reflux twice (the first time is for 2 hours and the second time is for 1.5 hours) at temperature 80-85° C. and steam pressure 0.1-0.2 MPa. The condensate is then filtered by the 120-mesh filter to discard the residue. The ethanol is then recollected from the filtrate by evaporation at 70° C. and steam pressure 0.15 MPa. The concentration process is ended when the relative density is 1.2-1.3 at 60° C. The concentrated extraction paste is transferred to the 300,000 grade clean area and then dried in vacuum of −0.07 MPa at 80° C. and steam pressure 0.2 MPa. The dry paste is finally ground into powder with the extraction yield of 10% and stored in the 300,000 grade clean area. The ethanol used in the extraction process may be collected.

*Ginkgo biloba* Leaf Extraction Process.

Figure 2:
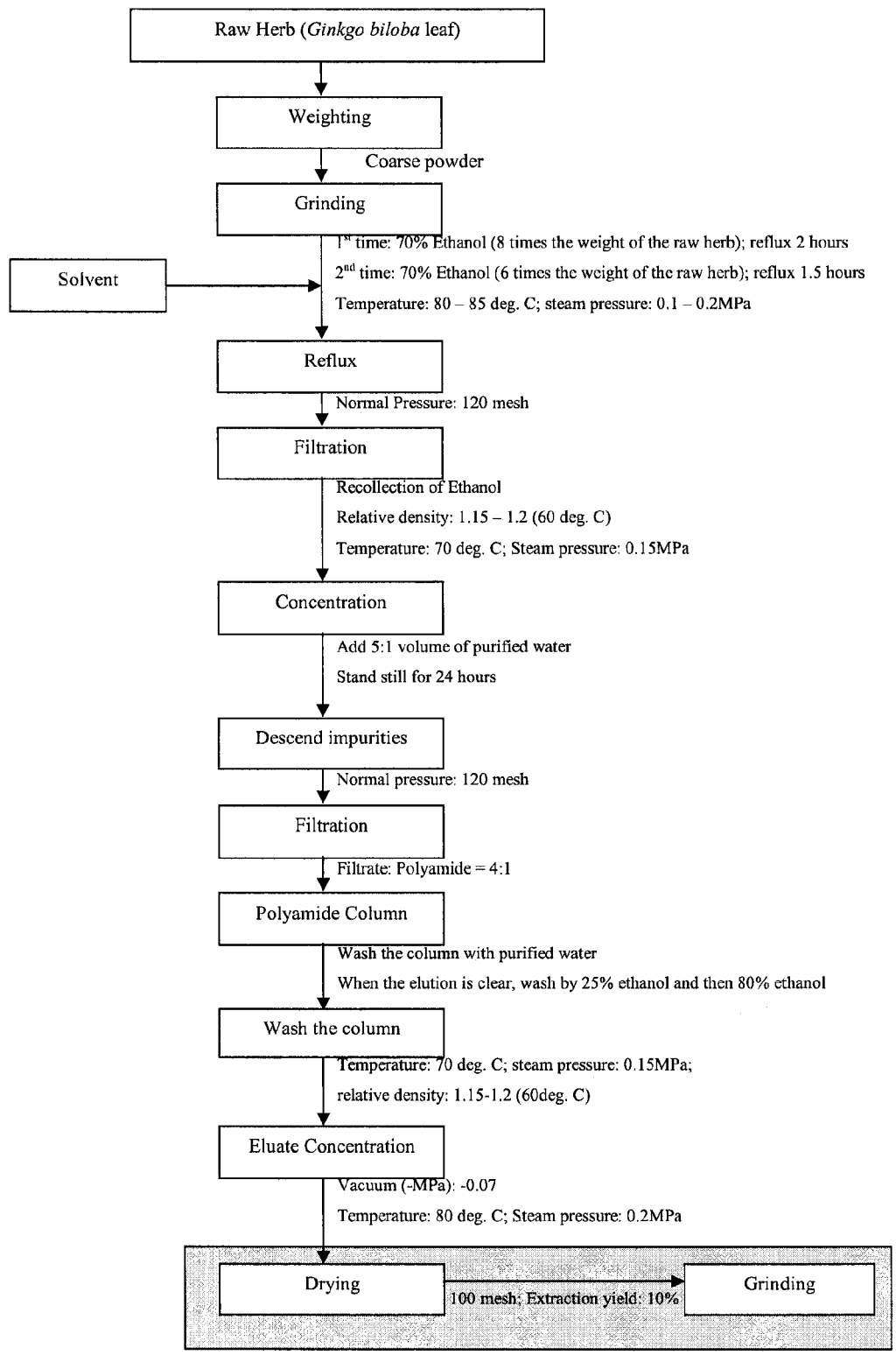
FIG. 2 is a flow chart representing an extraction process for *Ginkgo biloba* leaf.

A schematic version of one process of this extraction process is shown in FIG. 2. The *Ginkgo biloba* leaf raw herb is weighed and ground into coarse powder. The powder is then put into an extraction chamber. The herbal powder is heated under reflux twice with 70% ethanol. The first time: add 8:1 (w/w) 70% ethanol to the herb and heat under reflux for 2 hours. The second time: add 6:1 (w/w) 70% ethanol to the herb and heat under reflux for 1.5 hours. The temperature is 80-85° C. and steam pressure 0.1-0.2 MPa. After the reflux, the condensate is filtered under normal pressure and 120-mesh, and the residue discarded. Ethanol is recollected from the filtrate and concentrated again, at temperature 70° C., steam pressure 0.15 MPa. The concentration process is stopped when the relative density reaches 1.15-1.2 (at 60° C.). Then 5:1 (w/w) purified water is added to the filtrate and left of stand still for 24 hours. The filtrate is run on the polyamide column (filtrate:Polyamide=1:4). Purified water is added to wash the column until the eluate becomes clear. After that, 25% ethanol is added and then 80% ethanol is added to wash the column. The eluate is collected and concentrated at 70° C. and steam pressure 0.15 MPa. The concentrated extraction paste is transferred to the 300,000 grade clean area and then dried in vacuum of −0.07 MPa at 80° C. and steam pressure 0.2 MPa. The dry paste is finally ground into powder with the extraction yield 10% and stored in the 300,000 grade clean area.

EXAMPLES

Example 1

Analysis of Salidroside by High Performance Liquid Chromatography

Sample Preparation:

In liquid form: 20 ml of the sample solution is added to 25 ml methanol in a volumetric flask and is sonicated for 10 minutes. Afterwards, methanol is slowly added until the lowest part of the meniscus reaches the graduation mark of the flask and is then mixed thoroughly in the flask. Lastly, the solution is filtered with a 0.45 um filter.

In solid form: More than 20 tablets or capsules are ground into a powder. A given mass of the powder (accurate to 0.001 g) is put into a 50 ml volumetric flask. Methanol is added to the powder and the mixture is sonicated for 10 minutes. Next, methanol is added to the solution until its lowest meniscus reaches the graduation mark of the flask. The solution is then centrifuged at 3000 rpm for 3 minutes. The supernatent is collected and filtered with a 0.45 um filter.

HPLC Analysis:

A C18 column of 4.6 mm×250 (length) mm, and 5 um beads is used. The analysis is performed at room temperature. The mobile phase is 0.02 mol/L methanol in sodium acetate. Sample volume is 10 ul and flow rate is 1.0 ml/min. Detection is performed using a UV spectrophotometer at a wavelength of 215 nm. The Standard curve is prepared by analyzing different concentrations of a salidroside standard solution (0 ug/ml, 0.01 ug/ml, 0.02 ug/ml. 0.05 ug/ml, 0.2 ug/ml, and 0.5 ug/ml) by HPLC. The peak height/peak area comparison is used to set up the standard curve.

The collected data is analyzed using the following equation:

$$X = \frac{h_1 \times C \times V}{h_2 \times m \times 1000},$$

where X=amount of Salidroside in the sample (mg/g), $h_1$=Peak height/area of the sample solution; C=concentration of standard solution u/ml; V=volume of the sample solution; $h_2$=peak height/area of the standard solution, and; m=mass of the sample. X is corrected to 3 significant figures. The expected recovery rate is between 91.7% and 98.6%. For some herbal extractions, the absolute deviation of two individual test results (repeated under identical conditions) should not exceed 10% of their average values.

Example 2

Analysis of Flavonoids by HPLC

Sample Preparation:

A 0.5 g sample is weighed and 25 ml ethanol is added and then mixed by shaking. The solution is then sonicated for 20 minutes and then stands without agitation for a short period. One ml of the supernatant (clear fluid) is removed and added to an evaporation dish. One gram of polyamide powder is added. The ethanol from the solution is evaporated by placing the evaporation dish over a water bath set above room temperature. After evaporation, the residue is added to a chromatography column. 20 ml of benzene is added to wash the column. After washing, methanol is added to wash out the flavonoids before collecting 25 ml of elute. The absorbance of elute is measured by using a UV spectrophotometer (at wavelength: 360 nm). Meanwhile, a Rutin (flavonoid-containing) standard solution is used to prepare a standard curve for calculating the flavonoid amount in the sample.

Standard Curve Preparation:

5 mg Rutin (purchased from The National Institute for the Control of Pharmaceutical and Biological Products, Beijing, China) is added to 100 ml methanol to make a 50 ug/ml standard solution. Different dilutions of the standard solution (0 ug/ml, 5 ug/ml, 10 ug/ml. 15 ug/ml, 20 ug/ml, and 25 ug/ml) are prepared. The absorbance of the solutions is determined using a UV detector at wavelength 360 nm. The standard curve is plotted from the results, using the following formula:

$$X = \frac{A \times V_2 \times 100}{V_1 \times M \times 100},$$

where X=amount of flavonoids in the sample (mg/100 g); A=amount of flavonoids determined from the standard curve; M=mass of the sample (g); $V_1$=volume of the sample solution used in the test; $V_2$=total volume of the sample solution. X is corrected to 2 significant figures. For this extraction process, flavonoids should not be less than 800 mg/100 g.

Example 3

Manufacturing of *Rhodiola* and *Ginkgo* Extract Supplements

Raw materials (both the herbal ingredients and the excipients) are approved by the Quality Assurance Department before production is carried out. The ingredient powders (prepared as described above) are first accurately weighed according to a master formula with an electronic balance. The identity and quantity of each item to be weighed is verified. The weighed herbal ingredients and excipients are then loaded into a fluid bed dryer (Model number: GCTB-30; Changzhou Delson Pharmaceutical Machinery, Changzhou, China). Air flow is adjusted so that the powders are mixed sufficiently for 15-20 minutes. A moisturizing agent (75% ethanol) is then sprayed into the fluid bed dryer to allow the powder to granulate. During this process, the equipment inlet air temperature is maintained at 35-50° C. and the outlet air temperature at 25-30° C. After forming 20 mesh size granules, the granules are dried at 50±2° C.

The dried granules are then screened and sifted with an 18 mesh size stainless steel sieve by vibrating with screening machine (Model number: YK-160A; JiangYin Dry Equipment Co. Ltd., Jiangsu, China). Magnesium stearate is used as a lubricant and is added at 0.2% of the total weight of the granules. The powder is then mixed in a 3D motion mixer for 15 minutes. After being mixed sufficiently, 20 grams of the resulting powder is sampled for QC using an in-process control test for moisture (should be less than 5%).

After passing the QC in-process control test, the granules are transferred to a rotary tableting machine for tableting. The pressure, rotating speed and the tablet weight are adjusted so that each tablet weight reaches 0.4 g. The tablet fill weight and the intermediate product weight variation control range should be 0.4 g±7%. During the tableting process, 10 tablets are sampled and weighed for the total and individual weights every 20 minutes to check for weight variation. After tableting, 60 tablets are sampled for weight variation. Twenty tablets are subjected to a disintegration test (disintegrate within 30 minutes, or as required by target-country's regulations).

Film-coating of the tablets is carried out using a film-coating machine (Model number: GBB-600; Shanghai Zhong Lian Pharmaceutical Equipment, Shanghai, China). Film-coating solution is prepared by combining a pre-mixed film-coating agent (prepared in accordance with the standard Q/WS-2693-2001 in the Guangdong Provincial Drug Approval Notice (2001) #934001) and 50% ethanol. The ratio between the pre-mixed film-coating agent and 50% ethanol is 1:7. The amount of coating (by weight) should not exceed 3-6% of the uncoated tablet weight. A sample of coated tablets are subjected to a disintegration test (disintegrate within 60 minutes, or as required by target-country's regulations). A sample of tablets may also be tested for ash content, heavy metal (arsenic, lead, mercury), microbes (total aerobic, *E. coli*, yeast and mold, pathogens), and/or pesticides.

The tablets are counted, filled into bottles and fitted with proper closures. The pack size is 60 tablets per bottle. During the internal packaging process, 3 bottles will be sampled on 3 occasions to test for seal integrity, count size, closure fitness.

Figure 3:
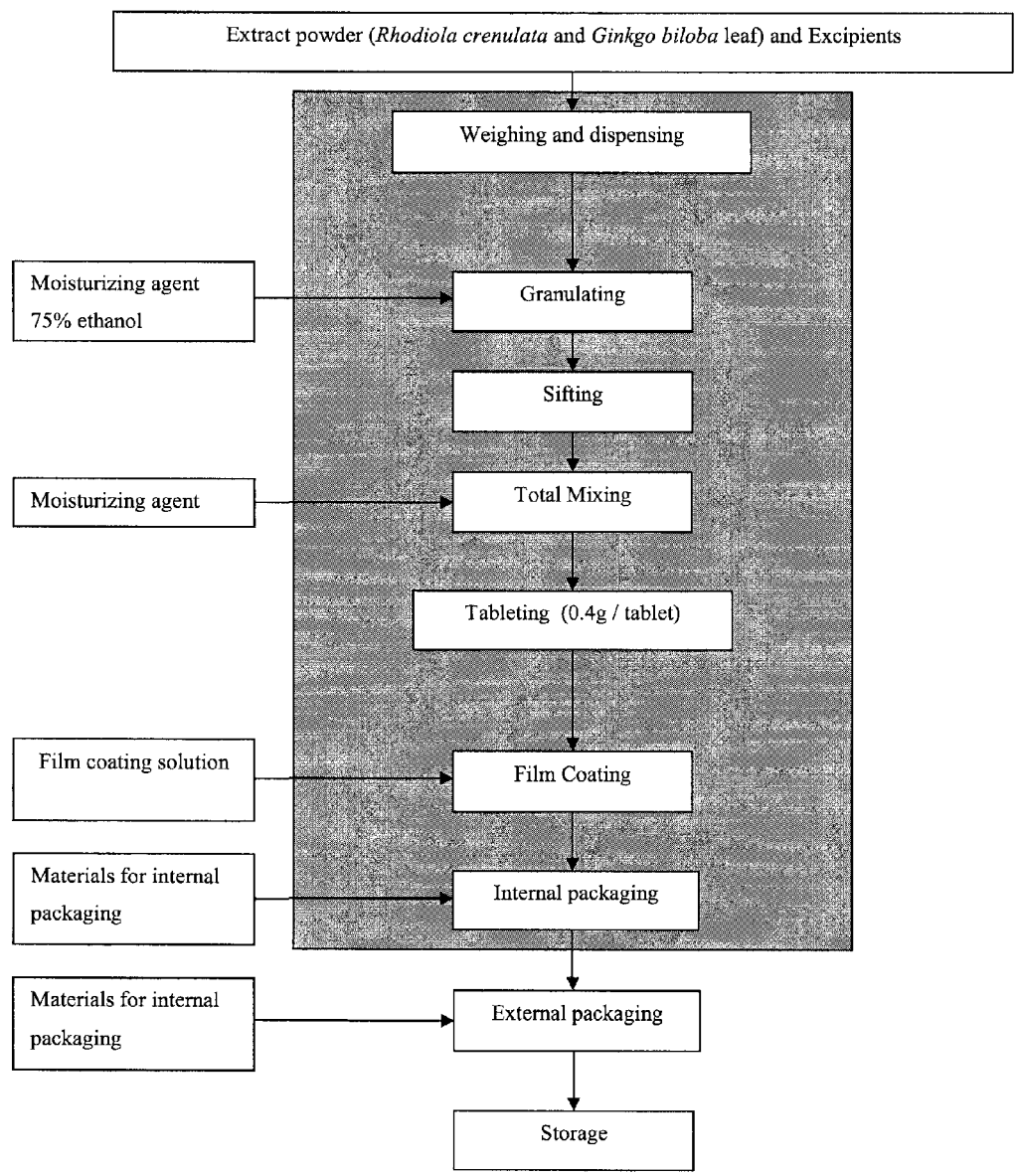
FIG. 3 is a flow chart representing a manufacturing process disclosed herein.

Filled bottles are affixed with labels imprinted with batch number and expiration date. Labelled bottles are then sealed with transparent full body sleeve shrink wrap. 100 bottles are packed into 1 carton. 7 bottles are sampled on three occasions to test for batch number and expiration date, label position, shrink wrap position, fitness, smoothness, cleanliness and integrity. After passing the QC test, the product will be released as finished products and properly stored. A schematic version of this process of supplement manufacture is shown in FIG. 3.

Example 4

*Rhodiola crenulata* and *Ginkgo biloba* Enhances Endurance Performance in Healthy Volunteers Empirical evidence has implicated that many herbal medicines possess athletic performance-improving potentials. This study was designed to determine whether the ingestion of an herbal supplement called *Rhodiola-Gingko* Capsule (RGC) would enhance endurance performance of healthy volunteers and change relevant hormones in a favorable manner.

Subjects and Estimation of Sample Size:

In order to minimize variations in demographic and baseline variables, the recruitment of subjects was limited to non-professional, college-level sportsmen who met the following criteria: 1) aged 18-22 years; 2) had moderate-intensity exercises in a regular manner, defined as doing exercises 5-7 hours per week; and 3) whose maximal oxygen uptake ($VO_{2max}$) and body mass index (BMI) were 47-75 mL·min$^{-1}$·kg$^{-1}$ and 18.5-26, respectively. Those who had unstable medical conditions, a history of alcohol or substance abuse within 1 year prior to the study, allergies to herbal medicines, needle phobia, or were currently under herbal or conventional medications were excluded from this study.

The present study was intended to detect a minimum 25% difference between RGC and placebo-treated groups in endpoint-to baseline change in $VO_{2max}$, with a power of $(1-\beta)=$ 90% and a two-side level of $\alpha=0.05$, using t-test or analysis of variance (ANOVA) model. Based on these assumptions, about 30 subjects per group were needed and the number increased to nearly 35 per group when 15% of participants were expected to be dropouts. Thus, seventy college-level sportsmen (18-22 years old) who had regular, moderate-intensity exercises were selected and randomized to ingest RGC (4 capsules/day, 400 mg herbal extracts/capsule, n=35) or equivalent placebo (n=35) for 7 weeks under double-blind condition. Endurance exercise tests were conducted at baseline, week 4, and endpoint.

Preparation of RGC and Placebo:

RGC and equivalent placebo used in the study were manufactured by Integrated Chinese Medicine Holdings of Hong Kong, by which RGC has been registered as a dietary supplement in the State Food and Drug Administration of China (registered number: G20060716; trademark: Sportchi™). RGC is formulated with *Rhodiola crenulata* and *Ginkgo biloba* leaves in a ratio of 9:1 in dry weight. The identification and extraction of both herbs were processed as described in *Pharmacopoeia of the People's Republic of China, PHARMACOPOEIA COMMISSION OF CHINA* (ed.); Chemical Industry Press, 2005. The extracted powder of both herbs was fully mixed and formed into dark orange, nontransparent capsules each containing 270 mg mixed extractives. The placebo was prepared with starchy powder in capsules identical to the active capsules in shape, size, and color.

To evaluate the quality of the preparation, the content of salidroside and flavonoids contained in the active capsules was measured using high-performance liquid chromatography (HPLC) and showed 23.80 mg/g and 12.55 mg/g extracted powder, respectively, much higher than the standards set in the *Pharmacopoeia of the People's Republic of China, PHARMACOPOEIA COMMISSION OF CHINA* (ed.); Chemical Industry Press, 2005. The content of heavy metals, insecticides, stimulants, narcotics, $\beta$ blockers, diuretics, and steroid hormones was undetectable or below the standards required.

Study Design and Procedures:

A double-blind, randomized, placebo-controlled design was used in the study. Participants were randomly assigned to receive RGC or placebo supplement in the ratio of 1:1 for 7 weeks in double-blind fashion, i.e., either participants or investigators (including capsule dispensers) were unaware of supplement conditions during the entire course of the study (supplement codes were kept with the manufacturer and not disclosed until the completion of data input). Each participant was required to take 4 capsules per day (2 after breakfast and 2 after supper). Assigned investigators directly dispensed capsules to each participant and monitored their ingestion on a daily basis. Participants were also asked to record their daily dietary, exercise and sleep patterns as well as incidence of adverse events. Endurance exercise tests were conducted at baseline (pretreatment), week 4, and endpoint (after completion of the treatment). All data was recorded in the data report form designed.

Endurance Exercise Tests:

Each subject was asked to perform a set of endurance exercise tests consisting of a 30-sec fixed workload test and a maximal incremental test at baseline (before treatment), week 4, and endpoint (after completion of treatment). The subjects were instructed to avoid strenuous exercises for 24 h before each test session and to arrive at the exercise testing laboratory in the rested and fully hydrated state. Food, caffeine, and alcohol intake was prohibited for 3 h before testing. The laboratory was maintained at 19-21° C. and 40-60% relative humidity during exercise testing. Each subject was tested at the same time on testing days to control circadian and diurnal influences.

30-sec fixed workload test: The test was conducted on a cycloergometer (Monark 834) to measure parameters associated with the power output. The test started with a warm-up without workload, through which 150-160 beat/min of heart rate was required to be achieved (3-5 min). Following this warm-up, subjects performed maximal cycling exercise with a fixed workload equal to 7.5% of body weight for 30 sec. Maximal power output ($W_{max}$), minimum power output (Wmin), mean power output ($W_{mean}$) and drop rate of the power output ($W_{drop}$) were measured based on a 5-sec interval data record.

Maximal incremental test: About 30 minutes after the completion of the fixed workload test, subjects started the maximal incremental test. Time to exhaustion and $VO_{2max}$ were measured in the test. The test was conducted on a motorized treadmill running machine (h/p/cosmos, Germany) using a standard Bruce Protocol (Baba et al., *J. Am. Coll. Cardiol.* 286:1567-1572, (1996)). Briefly, the slope of the treadmill was set at 10% with a speed of 1.7 mph in the initial 3 minutes of the test. The two parameters were then increased by 2% and by 0.5-0.9 mph every 3 minutes, respectively. Gas exchange of subjects' breath was analyzed continuously using an automated gas exchange analyzer (Max II, USA) through a facemask. Heartbeat was measured using a wireless heart rate monitoring method (Polar, Sweden). The test was stopped and exhaustive time and $VO_{2max}$ were recorded when any two of the following maximal criteria occurred: $VO_2$ plateau, respiratory exchange ratio (RER)>1.15, or heart rate>180 beat/min; or when the subject was exhausted and could not maintain the imposed treadmill speed.

Determination of Blood Testosterone and Cortisol Under Resting Condition:

Two 8-ml blood samples were collected under resting condition in the morning (7:00-8:00 AM), before meal at baseline and endpoint, respectively. Sera were immediately separated and stored at −80° C. for assay. Serum concentrations of testosterone (T) and cortisol (C) were measured using radioimmunoassay (RIA) and ratios of testosterone (nmol/L) to cortisol (μmol/L) was calculated. In order to exclude inter-assay variations, all samples were processed in one "batch" with the same assay kit under the same condition.

Statistical Analysis:

In order to exclude the influences of basal variations in endurance exercises, changes in endurance variables at week 4 and endpoint from baseline were used for statistical analysis. Baseline variables were analyzed using Student t-test. Two-way repeated measure analysis of variance (ANOVA) was used to detect main effects of supplement and treatment time on endurance and hormone parameters. Pairwise multiple comparisons were further conducted with Students-Newman-Keuls method if significant main effects were present. Data were expressed as mean±standard deviation (SD) unless otherwise indicated. All tests were two-sided and statistical significance was defined as p<0.05.

Subject Disposition and Characteristics:

A total of 70 sportsmen participated in the study and were randomly assigned to placebo (n=35) or RCG supplement (n=35). One participant initially assigned to placebo was removed from data analysis because his age did not reach the criterion (only 17 years old). Two participants allocated to RCG were excluded due to BMI value (26.4) higher than the criterion and incomplete endurance exercise tests, respectively. Nearly 95% of participants had moderate-intensity exercise for 1-2 hours in most days during the study. Nearly 82-85% of participants of each group slept for 6-8 hours nightly during the study. Almost all participants defined as their dietary pattern for mixed vegetable and meat. Baseline demographic and endurance exercise variables are shown in Table 1 and Table 2. No statistically significant differences were observed on baseline variables between the two groups.

TABLE 1

Demographic characteristics of subjects

| Variable | Placebo (n = 34) | RGC (n = 33) | p value[a] |
|---|---|---|---|
| Age (yr) | 20.0 (1.3) | 19.9 (1.0) | 0.748 |
| Height (cm) | 175.7 (4.6) | 174.7 (4.5) | 0.367 |
| Weight (kg) | 67.2 (7.1) | 65.2 (6.1) | 0.223 |
| BMI | 21.7 (1.7) | 21.3 (1.9) | 0.379 |

[a]Student t-test was used to detect statistical significance between the two groups.

TABLE 2

The effects of 7-week supplement with placebo and RGC on changes in endurance exercise tests at week 4 and endpoint from baseline values in college-level sportsmen

| Variables | Baseline | | | Changes at week 4 | | Changes at endpoint | |
|---|---|---|---|---|---|---|---|
| | Placebo | RGC | p value[a] | Placebo | RGC | Placebo | RGC[b] |
| Time to exhaustion (sec) | 801.6 | 794.1 | 0.654 | −7.5 | 7.1 | −9.7 | 10.3 |
| | (71.7) | (65.1) | | (39.0) | (36.4) | (38.2) | (46.2)* |
| $VO_{2max}$ (mL · min$^{-1}$ · kg$^{-1}$) | 62.0 | 59.5 | 0.101 | 1.4 | 3.2 | 0.4 | 3.9 |
| | (6.1) | (6.5) | | (6.7) | (6.1) | (6.4) | (5.2)* |
| peak power output | 10.1 | 10.0 | 0.963 | −0.1 | −0.2 | 0.0 | 0.0 |
| (W · kg$^{-1}$) | (1.7) | (0.8) | | (1.6) | (1.2) | (1.6) | (1.5) |
| Minimum power output | 5.8 | 5.5 | 0.237 | −0.4 | 0.0 | −0.3 | −0.3 |
| (W · kg$^{-1}$) | (0.9) | (0.9) | | (1.0) | (1.3) | (1.0) | (1.0) |
| Average power output | 7.7 | 7.6 | 0.449 | −0.2 | −0.1 | −0.2 | −0.2 |
| (W · kg$^{-1}$) | (0.7) | (0.5) | | (0.9) | (1.0) | (0.7) | (1.0) |
| power drop (W · sec$^{-1}$ · kg$^{-1}$) | 0.2 | 0.1 | 0.183 | 0.0 | 0.0 | 0.0 | 0.0 |
| | (0.1) | (0.1) | | (0.2) | (0.1) | (0.2) | (0.1) |

[a]Student t-test was used to detect statistical differences in basal values between placebo- (n = 34) and RGC-ingested subjects (n = 33).
[b]Two-way repeated measure ANOVA was conducted and followed by multiple group comparisons. *P < 0.05 vs. placebo group at the same time point.

Effects on Endurance Exercise Parameters:

The results of endurance exercise tests are summarized in Table 2. Two-way repeated measure ANOVA revealed a significant effect of treatment ($F_{1,66}$=4.480, P=0.038), but not treatment time ($F_{2,65}$=0.01, $^-$P=0.995), on changes in time to exhaustion from baseline. Multiple comparisons further revealed that the extension of time to exhaustion in RGC-treated subjects was significantly greater than placebo at endpoint (P=0.012).

Figure 4:
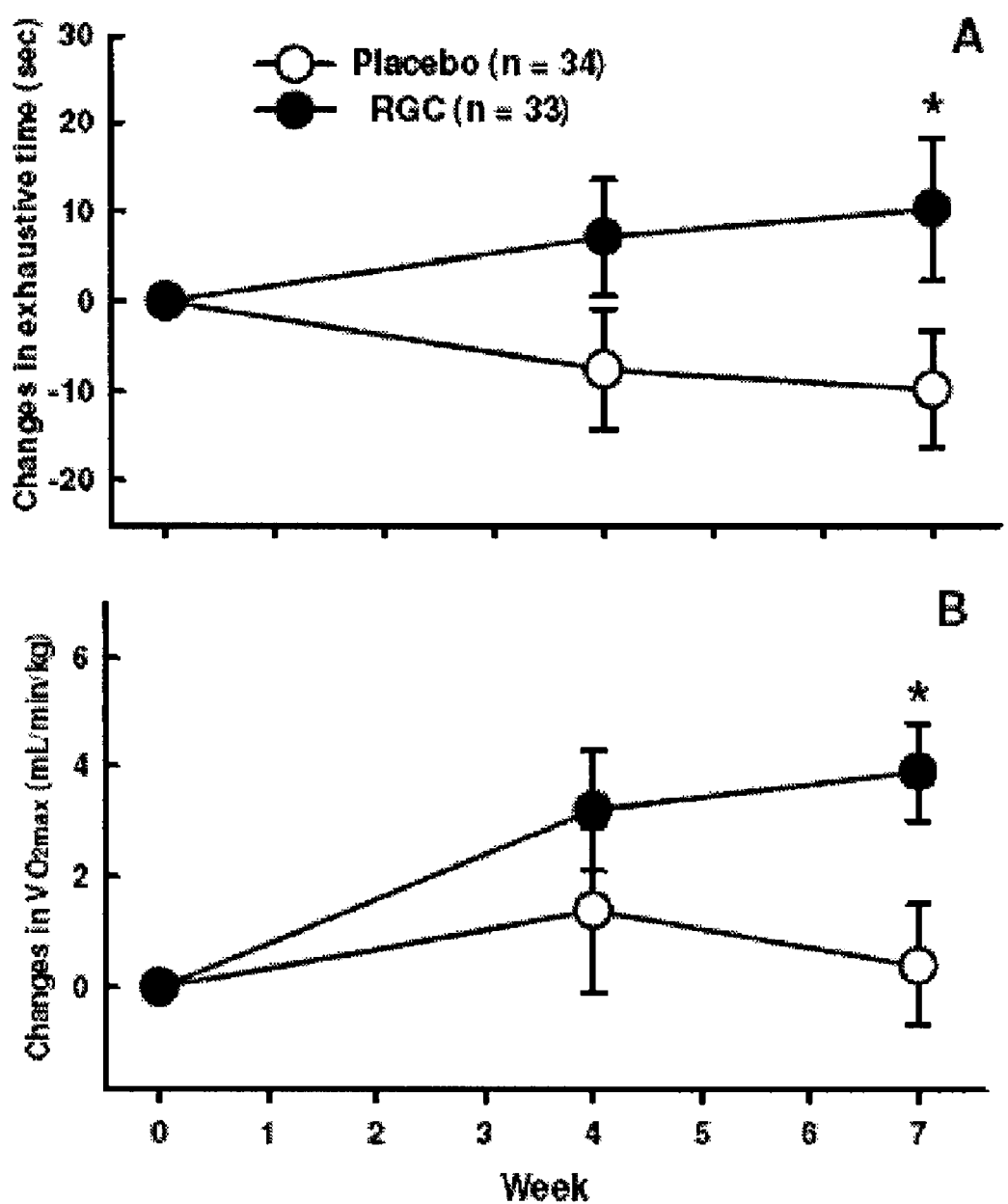
FIG. 4 depicts graphs representing the effects of 7-week supplement with placebo and RGC on changes from baseline in time to exhaustion (A) and $VO_{2max}$ (B) in maximal incremental test. Data are expressed as mean±standard error mean (SEM) and analyzed using two-way repeated measure ANOVA, followed by multiple group comparison. * $P<0.05$ vs. placebo values.

There were significant effects of both treatment ($F_{1,66}$=4.081, P=0.047) and time ($F_{2,65}$=6.955, P=0.001) on increases in $VO_{2max}$ from baseline. Multiple group comparisons further revealed that the amplitude of the increased $VO_{2max}$ in RGC-ingested subjects was significantly greater than placebo at endpoint (P=0.003). The increased amplitudes at week 4 and at endpoint were also significantly greater than baseline in RGC-ingested subjects (P<0.001), but not in placebo-ingested subjects (P>0.449) (FIG. 4).

Either treatment or time had no significant effects on changes in $W_{max}$ (treatment: $F_{1,66}$=0.101, $^{-1}$=0.751; time: $F_{2,65}$=0.562, P=0.576), $W_{min}$ (treatment: $F_{1,66}$=1.225, P=0.272; time: $F_{2,65}$=2.056, P=0.108), $W_{mean}$ (treatment: $F_{1,66}$=0.063, P=0.803; time: $F_{2,65}$=2.435, P=0.092), or $W_{drop}$ (treatment: $F_{1,66}$=1.508, P=0.224; time: $F_{2,65}$=0.745, P=0.477).

Figure 5:
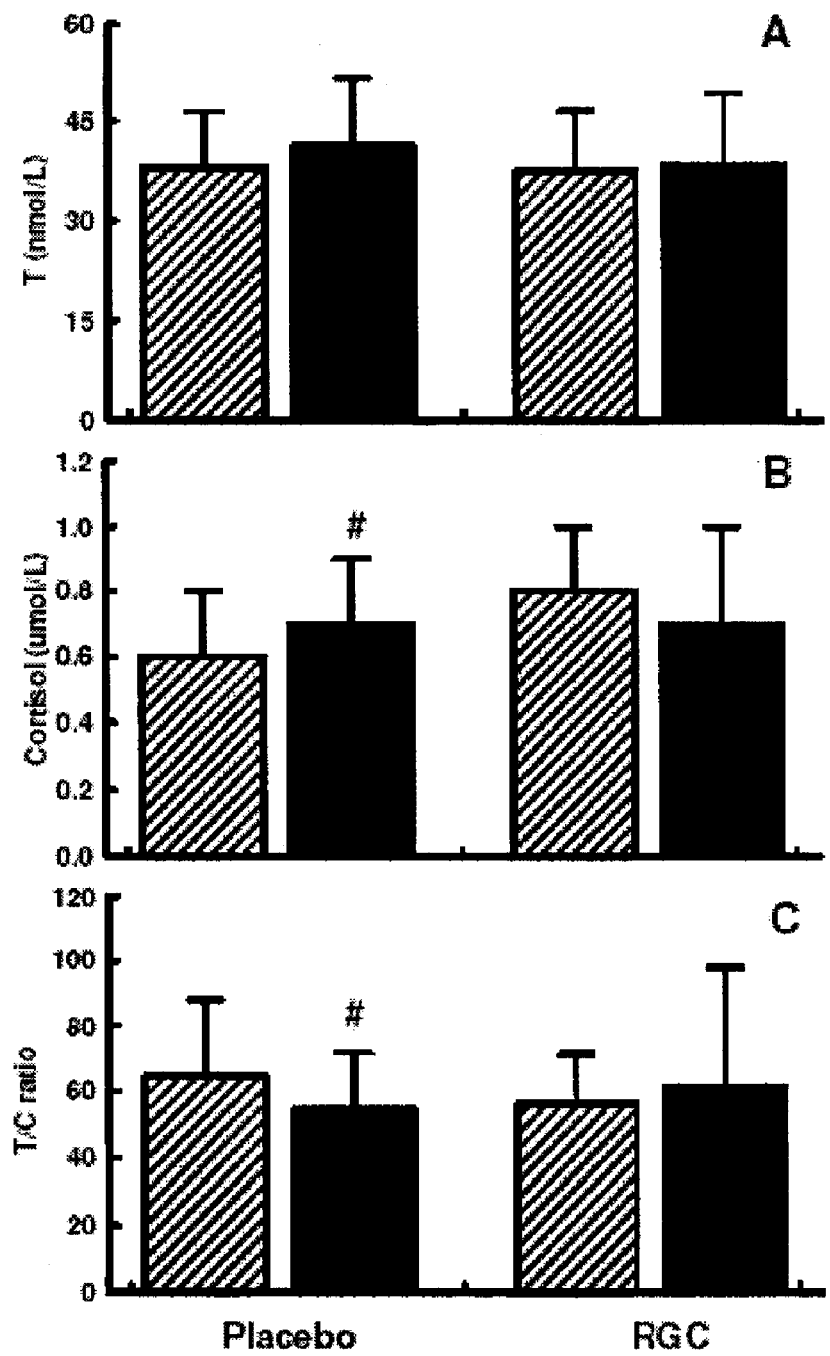
FIG. 5 depicts graphs representing the effects of 7-week supplement with placebo (n=34) and RGC (n=33) on testosterone (A), cortisol (B), and ratio of testosterone to cortisol (C) from baseline (stripped bars) to endpoint (filled bars). Data are expressed as mean±standard deviation (SD) and analyzed using two-way repeated measure ANOVA, followed by multiple group comparison. # $P<0.05$: vs. baseline values.

Effects on resting hormone levels: The effects on serum testosterone, cortisol concentrations and ratio of testosterone (nmol/L) to cortisol (μnmol/L) are illustrated in Table 3 and FIG. 5.

TABLE 3

The effects of 7-week supplements with placebo and RGC on serum hormones in college-level sportsmen[a]

| Variables | Baseline | | Endpoint | |
|---|---|---|---|---|
| | Placebo | RGC | Placebo | RGC |
| Testosterone (T, nmol/L) | 38.1 (8.4) | 37.4 (9.2) | 41.2 (10.6) | 38.4 (11.0) |
| Cortisol (C, μmol/L) | 0.6 (0.2) | 0.7 (0.2) | 0.8 (0.2)[#] | 0.7 (0.3) |
| T/C ratio | 64.6 (23.3) | 56.2 (14.8) | 54.5 (17.1)[#] | 61.3 (36.7) |

[a]Two-way repeated measure ANOVA was conducted to detect statistical significance in placebo-(n = 34) and RGC-ingested subjects (n = 33), followed by multiple group comparison.
[#]p < 0.05 vs. the same group at baseline.

The two groups of subjects had similar baseline serum concentrations of testosterone (t value=0.329, P=0.743), cortisol (t value=1.189, P=0.239), and T/C ratio (t value=1.758, P=0.083). No significant effects were observed on testosterone by either treatment ($F_{1,66}$=0.765, P=0.385) or time ($F_{2,65}$=2.565, P=0.114). Time factor had a significant effect on cortisol ($F_{1,65}$=10.845, P=0.002), but treatment factor did not ($F_{1,65}$=0.003, P=0.957). Multiple comparisons further showed that the mean cortisol level was significantly higher at endpoint than baseline in placebo-ingested subjects (P<0.001), but similar between the two time points in RGC-ingested subjects (P=0.294). A significant effect on the ratio was observed on time ($F_{1,65}$=5.096, P=0.027), but not on treatment ($F_{1,65}$<0.001, P=0.983). Multiple comparisons displayed a significant baseline-to-endpoint decrease in the ratio in placebo-ingested subjects (P=0.029), but not in RGC-ingested subjects (P=0.339).

Adverse Events:

There were 9 subjects (4 in placebo and 5 in RGC) who experienced transient sleepiness in the initial phase of treatment. No other adverse events were reported.

Summary:

The present study represents a methodologically rigorous investigation evaluating the efficaciousness of the herbal supplement prepared from a combination of *Rhodiola crenulata* and *Ginkgo biloba* in improving endurance exercise performance in comparison with placebo. In order to heighten the sensitivity and validity of the study, a highly uniform population was defined, characterized by the same gender, similar demographic, exercise, dietary and sleep patterns.

The present study found that the ingestion of RGC for 7 weeks resulted in an approximately 10-fold greater increase of $VO_{2max}$ from the baseline compared to placebo. Moreover, while placebo-treated subjects showed a shorter time to exhaustion at endpoint (nearly 10-second shorter than baseline), RGC-treated subjects displayed a remarkable extension of exhaustive time (about 10 seconds increased from baseline), yielding a significant difference between the two groups at endpoint (see Table 3 and FIG. 4), although indices associated with power output were unaffected. On the other hand, it is well known that cortisol excess and a decreased ratio of testosterone to cortisol are important indicators for overtraining and fatigue in endurance exercises (Urhausen and Kindermann, *Sports Med.* 32:95-102, (2002); Reilly and Ekblom, *J. Sports Sci.* 23:619-627, (2005)). In the present study, we found that, while placebo-ingested subjects displayed the significantly increased level of blood cortisol and the significantly decreased ratio of testosterone to cortisol under resting condition, the two hormone indices remained unchanged in RGC-ingested subjects following 7 weeks of treatment. These findings suggest that RGC possesses endurance-enhancing and anti-fatigue effects, protecting against declines in endurance performance; and the effects are largely achieved by increasing oxygen consumption.

Example 5

Cellular Effects of *Rhodiola crenulata* and *Ginkgo biloba*

To determine whether the combination of *Rhodiola crenulata* and *Ginkgo biloba* extracts has effects at the cellular level, in vitro tests were performed. RG, composed of 90% *Rhodiola crenulata* with 10% *Ginkgo biloba*, (batch #: 071001, Hong Kong Health Care Association Ltd), *Rhodioloa Crenulata* (batch #: HJ070202-H, Hong Kong Health Care Association Ltd), *Ginkgo biloba* (bath #: 060802, Hong Kong Health Care Association Ltd), and Vitamin C (Sigma, Co.) were used to treat L6 rat skeletal cells (L6) in DMEM media.

The data discussed below is represented by mean±SEM. Statistical analysis was performed using the two-tailed Student's t test for difference between samples. A difference with p<0.05 was considered statistically significant.

A) MTT Assay

L6 cells were cultured in 96-well tissue culture plates (1×10$^4$ cell/well) with 10% FBS for 24 hours. Serum-free medium was then used for another 24 hours prior to treatment with RGC, *Rhodiola crenulata* extract, or *Ginkgo biloba* extract. Cell viability and proliferation were measured by the 3-(4,5-dimethylthiazol-2-yl)-2,5-diphenyltetrazolium bromide (MTT) and 5-bromo-2'-deoxyuridine (BrdU) (Roche Diagnostics, USA) incorporation assays, respectively.

L6 cells were maintained in DMEM medium supplemented with 10% fetal calf serum, 100 U/ml penicillin and 100 U/ml streptomycin in a humid atmosphere of 5% $CO_2$ and 95% air at 37° C. The L6 cells were plated in 96-well plates (5000 cell/well) for 24 hours. Then the serum-free medium was used and cells incubated for another 12 hours. Sequentially, cells were pretreated with various concentrations (20 µg/ml, 40 µg/ml, 80 µg/ml) of RG, *Rhodiola Crenulata*, or *Ginkgo biloba*, respectively, or Vitamin C (80 µg/ml) for 12 hours, followed by exposure to an ischemic solution (EBSS) and placed in an anaerobic chamber (Diagnostic System) for 1 hour. The control cells were incubated without treatment for 1 hour. After 1 hour exposure to hypoxic and ischemic environments, 100 µl MTT (0.5 mg/ml in PBS) was added to each well and the cells were incubated at 37° C. for 4 h. The MTT solution was prepared by dissolving 250 mg of MTT in 50 ml PBS (0.01 mol/L, PH7.4) to prepare 0.5% MTT staining solution. The solution was then filtered through Millipore membrane and stored at 4° C.

Figure 6:
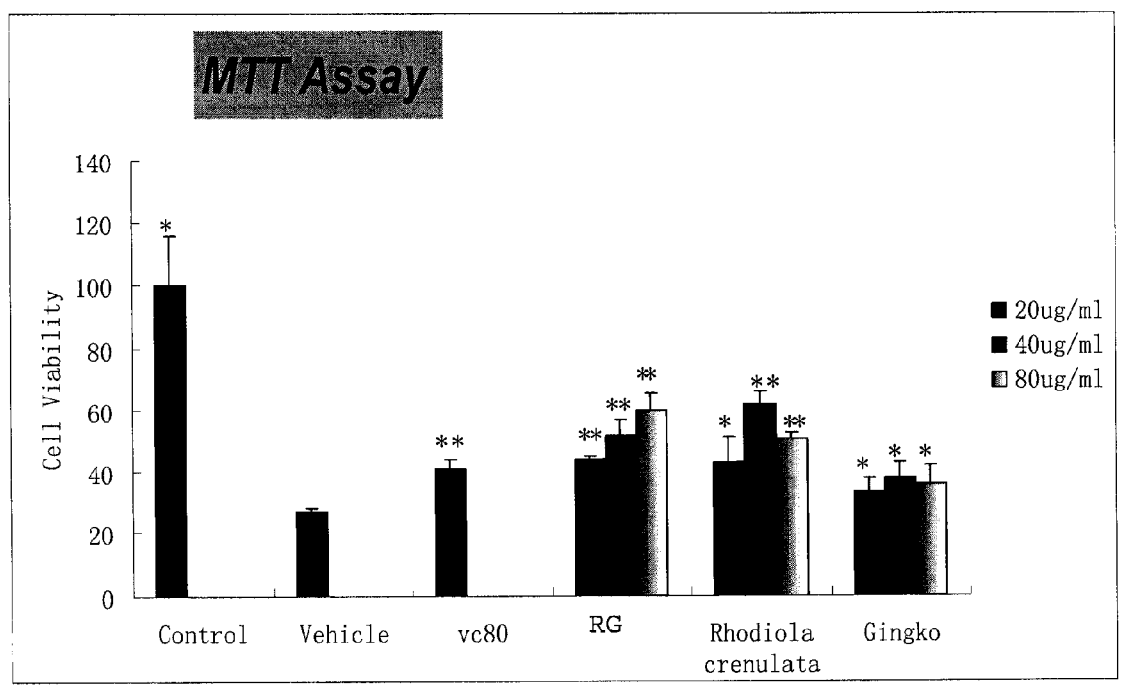
FIG. 6 depicts a graph of a MTT (3-(4,5-dimethylthiazol-2-yl)-2,5-diphenyltetrazolium bromide) Assay representing the effects of RG, *Rhodiola crenulata*, and *Ginkgo* on the viability of L6 cells under hypoxic conditions. Cell viability was measured by the MTT assay. Each histogram represents the mean with S.D. of 6 determinations. *, significantly different from vehicle at $P<0.05$; **, significantly different from vehicle at $P<0.01$.

The supernatants were removed carefully and 100 µl of dimethyl sulfoxide (DMSO) was added to each well to dissolve the precipitate. The absorbance at 570 nm was measured with a Infinite M200 microplate reader (TECAN) to evaluate the vitality of cells and as shown in Table 4 and FIG. 6. The cell proliferation in RGC, *Rhodiola crenulata* and *Ginkgo biloba* groups were significantly higher than that in the vehicle group under the hypoxic condition. The effect was dose-dependent. This indicated that RG, *Rhodiola crenulata* and *Ginkgo biloba* leaf extract has a protective effect to the rat skeletal muscle cells in hypoxic condition. RG (80 ug/ml) and *Rhodiola crenulata* (40 ug/ml) had a significant protective effect to the hypoxic rat skeletal muscle cell when compared with the *Ginkgo biloba* (40 ug/ml) ($p<0.01$).

TABLE 4

Cell proliferation in hypoxic conditions[a]

|  | 0 µg/ml | 20 µg/ml | 40 µg/ml | 80 µg/ml |
| --- | --- | --- | --- | --- |
| Vehicle | 27% ± 1.3% | N/A | N/A | N/A |
| RG | N/A | 44% ± 1.08%** | 52% ± 5.17%** | 60% ± 5.87%** |
| *Rhodiola crenulata* | N/A | 43% ± 8.14%* | 62% ± 4.19%** | 51% ± 1.9%** |
| *Ginkgo biloba* | N/A | 33% ± 4.9%* | 38% ± 4.8%* | 36% ± 6.0%* |
| Positive Control | N/A | N/A | N/A | 41% ± 3.2%** |

[a]The cell survival rate under hypoxic condition. Cell viability is measured by the MTT assay.
Data is presented as means ± SD.
*significantly different from vehicle at $P < 0.05$;
**significantly different from vehicle at $P < 0.01$.

B) LDH Assay

Trypan blue is one of several stains used for dye exclusion procedure for viable cell counting. The primary assessment of cell viability in this study is based on measurement of lactate dehydrogenase enzyme (LDH) leakage from the cells into the medium; an indicator of relative cell viability, using TOX-7 LDH based in vitro toxicology assay kit (Sigma, St Louis, USA). The LDH assay is measured spectrophotometrically at 490 nm.

L6 cells were maintained in DMEM medium supplemented with 10% fetal calf serum, 100 U/ml penicillin and 100 U/ml streptomycin in a humid atmosphere of 5% $CO_2$ and 95% air at 37° C. L6 cells were plated in 12-well plates ($4\times10^4$ cell/well) for 24 hours. Then the serum-free medium was used and cells incubated for another 12 hours. Sequentially, cells were pretreated with various concentrations (20 µg/ml, 40 µg/ml, and 80 µg/ml) of RG, *Rhodiola Crenulata*, or *Ginkgo biloba*, respectively, or Vitamin C (80 µg/ml) for 12 hours, followed by exposure to ischemic solution (EBSS) placed in an anaerobic chamber (Diagnostic System) for 1 hour. The control cells were incubated without treatment for 1 hour as well. Subsequently, the supernatants were removed and treated cells were washed with PBS followed 100 µl or lysis buffer. The cells were collected and centrifuged at 5000 r/min for 10 min at 4° C., the supernatant gathered and protein concentration determined using a BCA protein quantitative assay (BCA Protein Quantitative Analysis kit, available from Shanghai Biocolor Bioscience & Technology Company).

To prepare the protein standard curve for the BCA protein quantitative assay, 0, 0.5 µl, 1 µl, 2 µl, 4 µl, 6 µl, 8 µl, and 10 µl of diluted standard protein (0.5 mg/ml) was pipetted into wells and distilled water added to have a final volume of 20 µl for each well. Working solution was freshly prepared of which 200 ul was added in each well followed by incubated at 37° C. for 30 min. The absorbance at 562 nm was measured with a Infinite M200 microplate reader (TECAN) to calculate the standard curve. To determine the optimal sample volume for the BCA protein quantitative assay, various volume samples were diluted to the same final volume 20 µl then tested using BCA protein quantitative assay and the optimal sample volume chosen, 4 µl, was used in the BCA protein assay for the samples.

The optimal sample volume for LDH assay was determined by testing various volume samples that were diluted to the same final volume of 20 µl (see Tables 5 and 6). A LDH quantitative assay (commercially available LDH Assay Kits can be used) was then performed for each. The sample testing tubes were mixed well then placed in a water bath at 37° C. for 15 min. Then 50 µl dinitro-phenyl-hydrazine was added to each tube, mixed, and then placed in a water bath at 37° C. for 15 min. Next, 500 ul 0.4 mol/LNaOH was added to each tube and then left at room temperature for 3 min before detecting the absorbance at 440 nm. Volume-absorbance curve was acquired with sample volume as the X-axis while the absorbance as the Y-axis, and the volume between the linear range was chosen. 2 µl was selected as the best testing volume and used in for the LDH Assay.

TABLE 5

LDH pilot testing tubes

|  | Sample (µl) | | | | | |
| --- | --- | --- | --- | --- | --- | --- |
|  | 0 | 1 | 2 | 4 | 8 | 12 |
| Basis buffer (50 µl) | 50 | 50 | 50 | 50 | 50 | 50 |
| Distilled water (µl) | 20 | 19 | 18 | 16 | 12 | 8 |
| Coenzyme I (µl) | 10 | 10 | 10 | 10 | 10 | 10 |

TABLE 6

LDH pilot testing vehicle tubes

| | Sample (μl) | | | | | |
|---|---|---|---|---|---|---|
| | 0 | 1 | 2 | 4 | 8 | 12 |
| Basis buffer (50 μl) | 50 | 50 | 50 | 50 | 50 | 50 |
| Distilled water (μl) | 20 | 19 | 18 | 16 | 12 | 8 |
| Coenzyme I (μl) | 10 | 10 | 10 | 10 | 10 | 10 |

After optimal BCA assay volume and optimal LDH assay volumes were determined, the protein concentration and LDH activity for the samples of the various treatment groups (20 μg/ml, 40 μg/ml, or 80 μg/ml of RG, *Rhodiola Crenulata*, or *Ginkgo biloba*, respectively, and 80 μg/ml of Vitamin C) where the sample volumes were as shown in Table 7. The LDH activity assay was then performed where each sample was mixed and placed in a water bath at 37° C. for 15 min before 50 μl dinitro-phenyl-hydrazine was added to each tube. The samples were then mixed and placed in a water bath at 37° C. for 15 min. Next, 500 ul 0.4 mol/L NaOH was added to each tube and then left at room temperature for 3 min before detecting the absorbance at 440 nm. The LDH activity was calculated according to the formula: LDH activity (U/g protein)=(Testing OD−Testing vehicle OD)/(Standard OD−Standard vehicle OD)×Standard concentration/protein concentration (g of protein/ml) and is shown in Table 8 and FIG. 7.

TABLE 7

LDH activity assessment

| | St | St vehicle | Testing vehicle | Testing |
|---|---|---|---|---|
| Basis buffer (μl) | 50 | 50 | 50 | 50 |
| 2 μmol/L pyruvate (μl) | 2 | | | |
| Distilled water (μl) | 10 | 12 | 10 | |
| Sample (μl) | | | 2 | 2 |
| Coenzyme I (μl) | | | | 10 |

Figure 7:
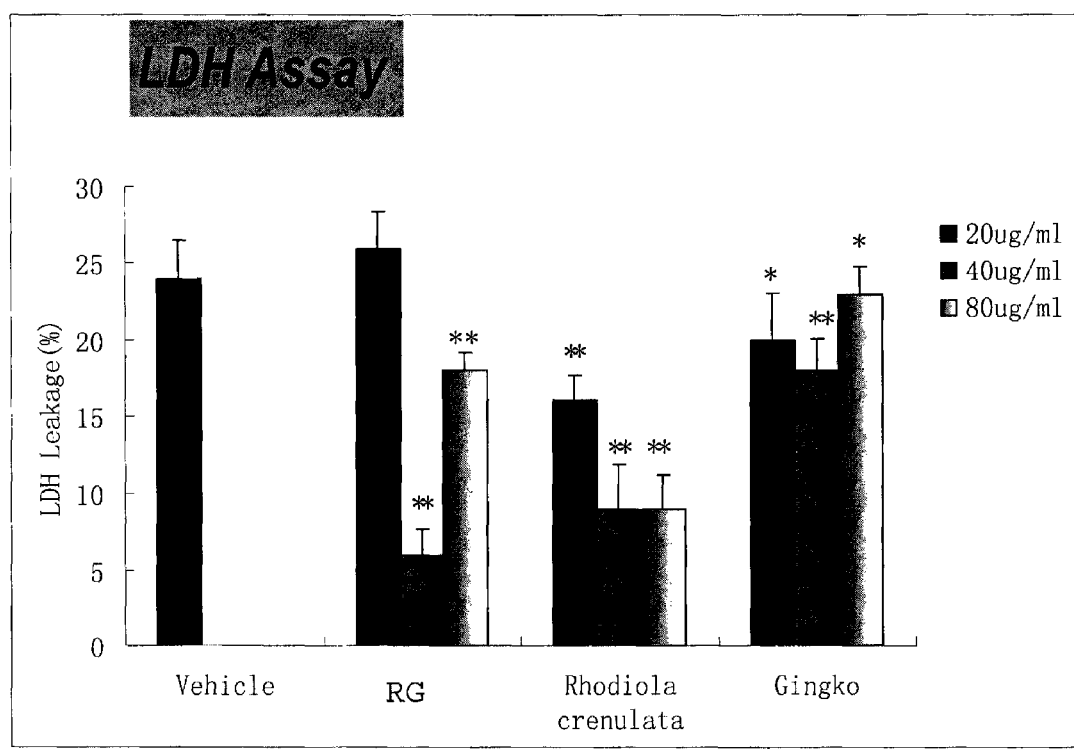
FIG. 7 depicts a graph of a LDH (lactate dehydrogenase) Assay representing the effects of RG, *Rhodiola crenulata*, and *Ginkgo biloba* on the LDH leakage of L6 cells under hypoxic conditions. LDH leakage was measured by the LDH assay. Each histogram represents the mean with S.D. of 5-6 determinations. *, significantly different from vehicle at $P<0.05$; **, significantly different from vehicle at $P<0.01$.

As shown in Table 8 and FIG. 7, the LDH leakage rate in RG, *Rhodiola crenulata* and *Ginkgo biloba* groups were significantly lower than that in the vehicle group under the hypoxic condition. This indicated that RG, *Rhodiola crenulata* and *Ginkgo biloba* leaf extract has a protective effect to the rat skeletal muscle cells in the hypoxic condition. RG (40 ug/ml) has significant protective effect to the hypoxic rat skeletal muscle cell when compared with the *Rhodiola crenulata* (40 ug/ml) (p<0.05) and *Ginkgo biloba* (40 ug/ml) (p<0.01), respectively. *Rhodiola crenulata* (40 ug/ml) also has significant protective effect to the hypoxic rat skeletal muscle cell when compared with the *Ginkgo biloba* (40 ug/ml) (p<0.01).

TABLE 8

LDH Leakage Rates[a]

| | 0 μg/ml | 20 μg/ml | 40 μg/ml | 80 μg/ml |
|---|---|---|---|---|
| RG | N/A | 26% ± 2.3%* | 6% ± 1.7%** | 18% ± 1.1%** |
| *Rhodiola crenulata* | N/A | 16% ± 1.7%** | 9% ± 2.9%** | 9% ± 2.22%** |
| *Ginkgo biloba* | N/A | 20% ± 3.1%* | 18% ± 2.1%** | 23% ± 1.8%* |
| Vehicle | 24% ± 2.6% | N/A | N/A | N/A |

[a]The LDH leakage of L6 cells under hypoxic condition. The LDH leakage is measured by LDH assay.
Data is presented as means ± SD.
*significantly different from vehicle at $P < 0.05$;
**significantly different from vehicle at $P < 0.01$.

C) SOD Antioxidant Assay

Cells were homogenized in ice-cold phosphate buffer (50 mmol/L, pH 7.4) to make 10% w/v homogenate with a motor-driven Potter-Elvejhem glass homogenizer at 0-4° C. The homogenate will be then centrifuged at 300 g for 10 min at 4° C. to remove intact cells and debris. The remaining supernatant was divided into 2 parts for different enzyme assays. For SOD assays, the supernatant will be centrifuged at 2300 g for a further 10 min at 4° C. After centrifugation, the pellets will be discarded and the supernatants were used for the assessment of enzyme activity. The procedure was carried out on ice or at 0-4° C. Reagents for the assay were obtained through a commercially available SOD Assay Kit. The optimal sample volumes for the BCA quantitative assay and the SOD assay were determined as described in the LDH assay.

After determination of optimal sample volumes, a pilot study was performed using the volumes as shown in Table 9. The samples were mixed and placed in a water bath at 37° C. for 40 min. A chromogenic agent (200 μl) was then added, the samples mixed, then left at room temperature for 10 min before absorbance at 550 nm was detected. The Inhibition ration was then calculated using the formula: Inhibition ratio=(ODn−OD1)/OD1×100%. The inhibition ratio between 48%-50% was considered as the optimal sample volume, and thus, 10 μl was selected for use for the SOD assays. The protein concentration was measured using the BCA protein quantitative assay.

TABLE 9

SOD pilot study

| | Sample (μl) | | | | | | |
|---|---|---|---|---|---|---|---|
| | 1 | 2 | 4 | 6 | 8 | 10 | 12 |
| | Water (μl) | | | | | | |
| | 1 | 2 | 4 | 6 | 8 | 10 | 12 |
| Reagent 1 (μl) | 100 | 100 | 100 | 100 | 100 | 100 | 100 |
| Reagent 2 (μl) | 100 | 100 | 100 | 100 | 100 | 100 | 100 |
| Reagent 3 (μl) | 100 | 100 | 100 | 100 | 100 | 100 | 100 |
| Reagent 4 (μl) | 100 | 100 | 100 | 100 | 100 | 100 | 100 |

After 10 μl was selected for use for the SOD assays, SOD activity assays were performed for the samples of the various treatment groups (20 μg/ml, 40 μg/ml, or 80 μg/ml of RG, *Rhodiola Crenulata*, or *Ginkgo biloba*, respectively, and 80 μg/ml of Vitamin C) where the sample volumes were as shown in Table 10. The samples were mixed and placed in a water bath at 37° C. for 40 min. A chromogenic agent (200 μl) was then added, the samples mixed, then left at room temperature for 10 min before absorbance at 550 nm was detected. The SOD enzyme activity was then calculated according to the formula: T-SOD activity (U/gprot)=(Control O.D.−Testing O.D.)/Control O.D./50%×total volume/sample volume/protein conc. (gprot/ml).

TABLE 10

SOD activity assay

|  | T-SOD control | T-SOD testing |
|---|---|---|
| Reagent 1 (µl) | 100 | 100 |
| Distilled water (µl) | 10 | 10 |
| Sample (µl) | 10 | 10 |
| Reagent 2 (µl) | 10 | 10 |
| Reagent 3 (µl) | 10 | 10 |
| Reagent 4 (µl) | 10 | 10 |

Figure 8:
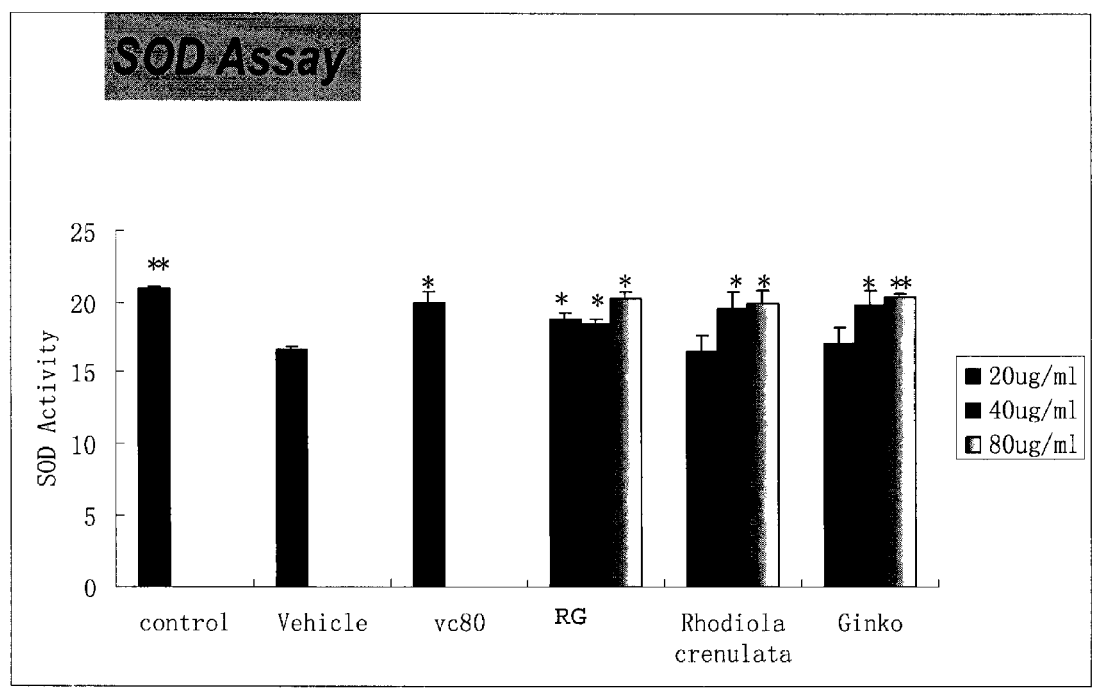
FIG. 8 depicts a graph of a SOD (superoxide dismutase) Antioxidant Assay representing the effects of RG, *Rhodiola crenulata*, and *Ginkgo biloba* on the SOD activity of L6 cells under hypoxic conditions. SOD activity was measured by the SOD assay. Each histogram represents the mean with S.D. of 5-6 determinations. *, significantly different from vehicle at $P<0.05$; **, significantly different from vehicle at $P<0.01$.

The results as shown in Table 11 and FIG. 8 reveal that SOD enzymatic activity in RG, *Rhodiola crenulata* and *Ginkgo biloba* groups are significantly higher than that in the Vehicle group.

TABLE 11

SOD Enzymatic Activity

|  | 0 µg/ml | 20 µg/ml | 40 µg/ml | 80 µg/ml |
|---|---|---|---|---|
| RG | N/A | 18.83% ± 0.47%* | 18.50% ± 0.27%** | 20.26% ± 0.54%** |
| *Rhodiola crenulata* | N/A | 16.48% ± 1.20%* | 19.61% ± 1.19%* | 19.98% ± 0.87%* |
| *Ginkgo biloba* | N/A | 17.09% ± 1.11%* | 19.79% ± 1.05%* | 20.36% ± 0.26%** |
| Vc | N/A | N/A | N/A | 20.00% ± 0.08%* |
| Vehicle | 16.58% ± 0.31% | N/A | N/A | N/A |
| Vehicle | 20.98% ± 0.11%** | N/A | N/A | N/A |

$^a$The SOD activity of L6 cells under hypoxic condition. The SOD activity is measured by SOD assay.
Data is presented as means ± SD.
*significantly different from vehicle at $P < 0.05$;
**significantly different from vehicle at $P < 0.01$.

Conclusions:

Chinese herbal extract RG (*Rhodiola crenulata* and *Ginkgo biloba*) enhances cell growth and proliferation in normoxic and hypoxic conditions. The study adopts MTT, LDH and SOD colorimetric assays. The MTT assay shows that the cell viability of cells treated with RG are higher than that of vehicles and negative controls under hypoxic conditions and the result shows dose-dependence. The LDH assay shows that the LDH leakage of cells treated with RG is lower than the Vehicle group. The SOD assay shows that the SOD activity of cells treated with RG are higher than the Vehicle group. The study shows that RG can promote the proliferation of the rat skeletal muscle cells and have anti-hypoxia and protective effects. Furthermore, the study also shows that RG has a much better effect than *Gingko biloba* alone and a greater effect than *Rhodiola crenulata* alone.

Example 6

Cellular Effects of *Rhodiola crenulata* and *Ginkgo biloba* on Human Cells

To determine whether the combination of *Rhodiola crenulata* and *Ginkgo biloba* extracts have effects at the cellular level in human cells, in vitro tests are performed. The tests are conducted by adding the combined extracts, the extracts individually, or no extract to human skeletal muscle cells in vitro and determining effects of several cellular functions. The expression of vascular endothelial growth factor (VEGF), myoglobin and citrate synthase genes, and SOD enzymatic activity, and cell proliferation and growth are measured under normoxic and hypoxic conditions. Increase in the gene expression of VEGF and myoglobin indicate improved capability to provide oxygen to the cells. Alternation of the citrate synthase encoding gene, a commonly used marker for the presence of intact mitochondria in muscle cells, indicates muscle adaptation to hypoxic conditions. Alternation (increase) of SOD enzymatic activity from the SOD antioxidant assay suggests increase in the oxidative capacity of the cells under hypoxic conditions.

Example 7

Cellular Effects of *Rhodiola crenulata* and *Ginkgo biloba* Combinations

To determine whether different ratios of extracts of *Rhodiola crenulata* and *Ginkgo biloba* have differing effects on cells, the following experiments were performed. Rat skeletal muscle cells L6 cells were maintained in DMEM medium supplemented with 10% fetal calf serum, 100 U/ml penicillin and 100 U/ml streptomycin in a humid atmosphere of 5% $CO_2$ and 95% air at 37° C. Rat Skeletal Muscle Cells L6 cells were plated in 6-well plates ($1 \times 10^5$ cell/well) for 24 hours. Serum-free medium was then used and cells incubated for another 12 hours. Sequentially, cells were pretreated with various concentrations groups for 12 hours. The groups were as follows: Group 1—80% *Rhodiola crenulata*+20% *Ginkgo biloba* (e.g. total 80 ug/ml), Group 2—80% *Rhodiola crenulata* (e.g. total 64 ug/ml), Group 3—100% *Rhodiola crenulata* (e.g. total 80 ug/ml), Group 4 ("RG" group)—90% *Rhodiola crenulata*+10% *Ginkgo biloba* (e.g. total 80 ug/ml); Group 5—90% *Rhodiola crenulata* (e.g. total 72 ug/ml), Group 6—Vit. C as control group, Group 7—Vehicle, Group 8—Control.

Each group was exposed to an ischemic solution (EBSS) and placed in an anaerobic chamber (Diagnostic System) for 2 hours. The control cells were incubated without treatment for 2 hours as well. The supernatants were then removed and the treated cells were washed with PBS followed 100 µl of lysis buffer. The cells were collected and centrifuged at 5000 r/min for 10 min at 4° C. The supernatant was then gathered and the protein concentration determined was using the BCA protein quantitative assay, as described in Example 5. The LDH activity (FIG. 9) and SOD activity (FIG. 10) were determined using methods as described in Example 5.

Figure 9:
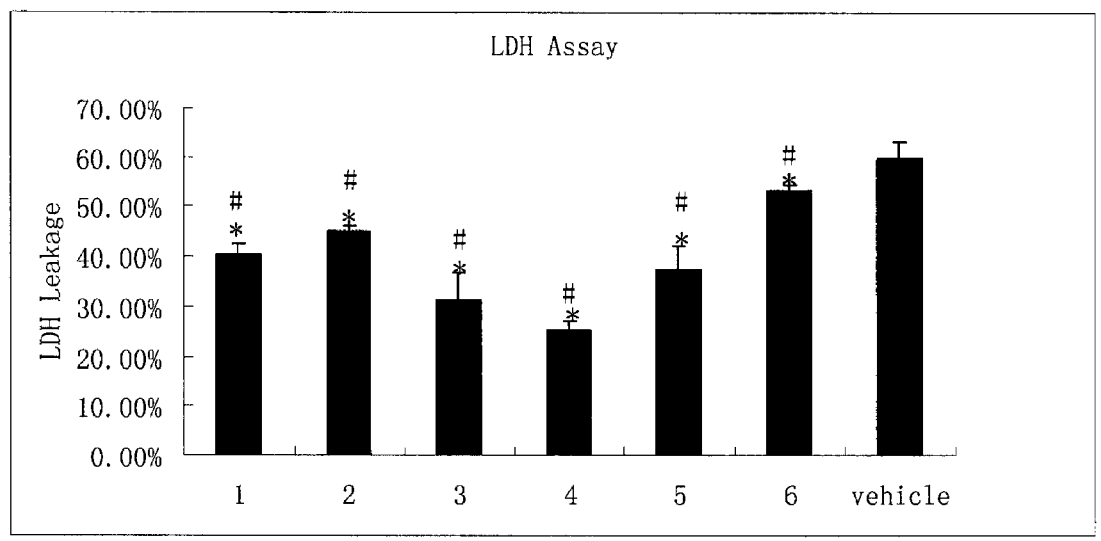
FIG. 9 depicts a graph representing the effects of RG, *Rhodiola crenulata*, and *Ginkgo biloba* on the SOD activity of L6 cells under hypoxic conditions. Group 1—80% *Rhodiola crenulata*+20% *Ginkgo biloba* (e.g. total 80 ug/ml), Group 2—80% *Rhodiola crenulata* (e.g. total 64 ug/ml), Group 3—100% *Rhodiola crenulata* (e.g. total 80 ug/ml), Group 4 ("RG" group)—90% *Rhodiola crenulata*+10% *Ginkgo biloba* (e.g. total 80 ug/ml); Group 5—90% *Rhodiola crenulata* (e.g. total 72 ug/ml), Group 6—Vit. C as control group, Group 7—Vehicle, Group 8—Control. LDH leakage for each group was measured by the LDH assay. Each histogram represents the mean with S.D. of 5-6 determinations. *, significantly different from vehicle at $P<0.05$; # significantly different from 4 at $P<0.05$.
Figure 10:
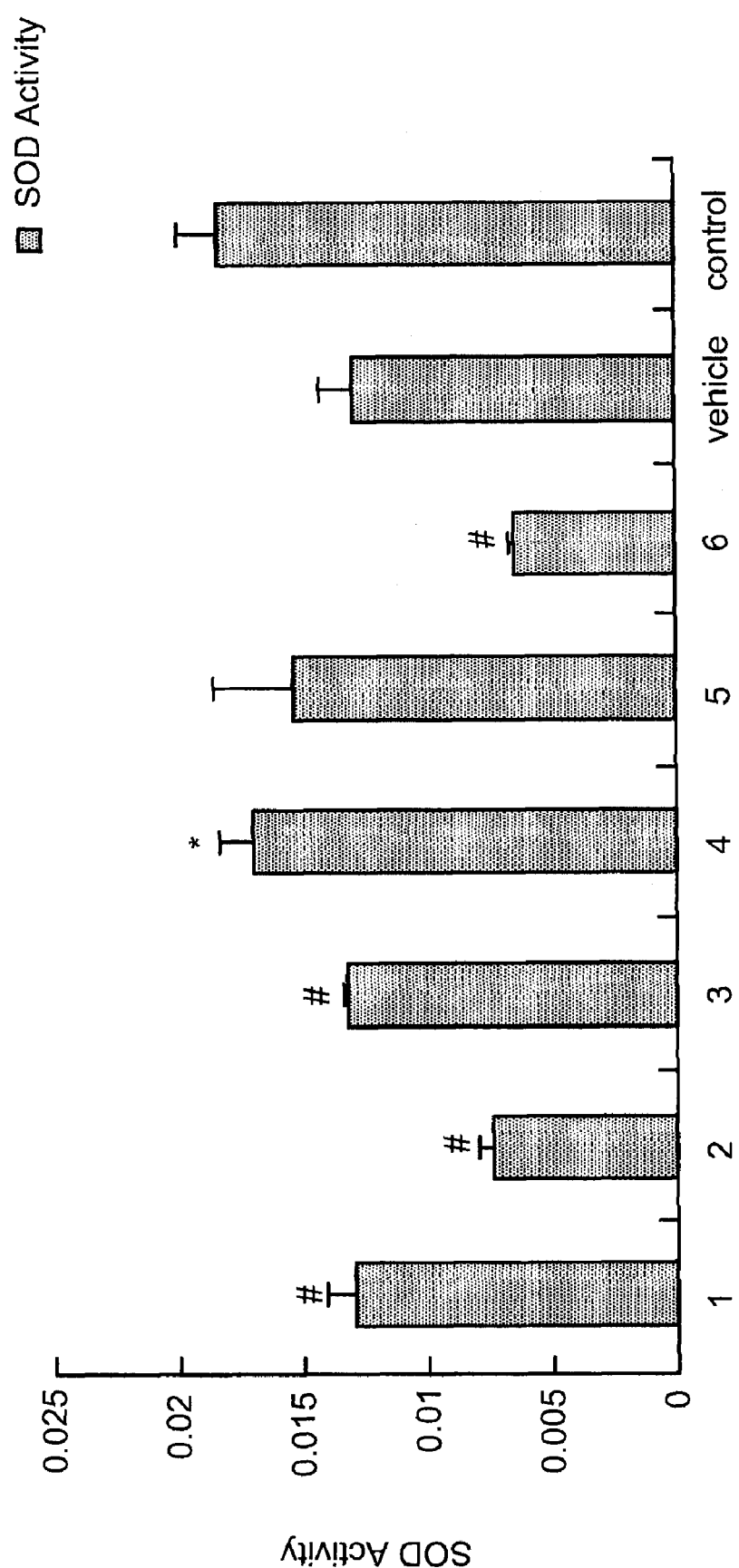
FIG. 10 depicts a graph representing the effects of Group 1 to Group 7 on the SOD activity of L6 cells under hypoxic conditions. Group 1—80% *Rhodiola crenulata*+20% *Ginkgo biloba* (e.g. total 80 ug/ml), Group 2—80% *Rhodiola crenulata* (e.g. total 64 ug/ml), Group 3—100% *Rhodiola crenulata* (e.g. total 80 ug/ml), Group 4 ("RG" group)—90% *Rhodiola crenulata*+10% *Ginkgo biloba* (e.g. total 80 ug/ml); Group 5—90% *Rhodiola crenulata* (e.g. total 72 ug/ml), Group 6—Vit. C as control group, Group 7—Vehicle, Group 8—Control. SOD activity was measured by the SOD assay. Each histogram represents the mean with S.D. of 5-6 determinations. *, significantly different from vehicle at $P<0.05$. # significantly different from 4 at $P<0.05$.

As shown in FIG. 9, the LDH leakage rate in Groups 1 to 6 are significantly lower than that in the Vehicle group under the hypoxic condition. In addition, Group 4 has a significant protective effect to the hypoxic rat skeletal muscle cell when compared with the other five groups. As shown in FIG. 10, SOD enzymatic activity in Group 3 and group 4 are significantly higher than that in Vehicle group. In addition, SOD enzymatic activity in group4 is significantly higher than those four groups except group5. This in-vitro study showed that group 4 (RG) have a significantly better anti-hypoxic effect than the other five groups in the rat L6 skeletal muscle cells.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A composition comprising about 90% w/w of a *Rhodiola crenulata* extract and about 10% w/w of a *Ginkgo biloba* extract based on the total weight of the composition, wherein the *Rhodiola crenulata* extract comprises at least about 0.10 w/w salidroside based on the total weight of the *Rhodioa crenulata* extract, and the *Ginkgo biloba* extract comprises at least about 0.10% w/w flavonoids based on the total weight of the *Ginkgo biloba* extract.

2. The composition of claim 1, further comprising one or more excipients.

3. The composition of claim 1, wherein the composition is a solid.

4. The composition of claim 1, wherein the composition is a liquid.

5. The composition of claim 1, wherein the herbal extract of *Rhodiola crenulata* comprises at least 1.0% w/w salidroside based on the total weight of the herbal extract.

6. The composition of claim 1, wherein the herbal extract of *Rhodiola crenulata* comprises 1.0%-5.0% w/w salidroside based on the total weight of the herbal extract.

7. The composition of claim 1, wherein the herbal extract of *Ginkgo biloba* comprises 0.10%-1.5% w/w flavonoids based on the total weight of the herbal extract.

8. A kit comprising at least one dose of an effective amount of the composition of claim 1.

9. The kit of claim 8, further comprising instruction of how to use the kit to improve or restore blood circulation, promote mental acuity, reduce fatigue, or promote aerobic or anaerobic performance.

10. The kit of claim 8, wherein more than one dose of an effective amount of the composition of claim 1 is included.

11. The kit of claim 8, further comprising a dispensing cup or a dispensing spoon.

12. A method for improving or restoring blood circulation in the body of a mammal comprising: administering to the mammal in need thereof an effective amount of the composition of claim 1.

13. The method of claim 12, wherein said administration is oral.

14. The method of claim 12, wherein the composition is administered to a human at a dose of about 1-3200 mg/day, about 400-2000 mg/day, about 800-1600 mg/day, about 1200-1600 mg/day, or about 1000 mg/day.

15. The method of claim 12, wherein the composition is orally administered to a human at a dose of about 1-100 mg/kg, about 1-60 mg/kg, about 1-30 mg/kg, about 1-15 mg/kg, about 1-6 mg/kg or about 1-5 mg/kg once or twice a day.

16. A method for reducing fatigue or promoting aerobic performance in a mammal comprising: administering to the mammal in need thereof an effective amount of the composition of claim 1.

17. The method of claim 16, wherein said administration is oral.

18. The method of claim 16 wherein the composition is administered to a human at a dose of about 1-3200 mg/day, about 400-2000 mg/day, about 800-1600 mg/day, about 1200-1600 mg/day, or about 1000 mg/day.

19. The method of claim 16, wherein the composition is orally administered to a human at a dose of about 1-100 mg/kg, about 1-60 mg/kg, about 1-30 mg/kg, about 1-15 mg/kg, about 1-6 mg/kg or about 1-5 mg/kg once or twice a day.

* * * * *